US011667694B2

(12) United States Patent
Weggeman et al.

(10) Patent No.: US 11,667,694 B2
(45) Date of Patent: Jun. 6, 2023

(54) THERAPEUTIC USES OF FIBRINOGEN GAMMA PRIME VARIANTS

(71) Applicant: FIBRIANT B.V., Leiden (NL)

(72) Inventors: Miranda Weggeman, Leiden (NL); Joseph Grimbergen, Leiden (NL); Jacob Koopman, Leiden (NL)

(73) Assignee: FIBRIANT B.V., Leiden (NL)

( * ) Notice: Subject to any disclaimer, the term of this patent is extended or adjusted under 35 U.S.C. 154(b) by 0 days.

(21) Appl. No.: 17/212,738

(22) Filed: Mar. 25, 2021

(65) Prior Publication Data

US 2021/0347853 A1 Nov. 11, 2021

Related U.S. Application Data

(63) Continuation of application No. 16/716,172, filed on Dec. 16, 2019, now abandoned, which is a continuation of application No. PCT/EP2019/060546, filed on Apr. 24, 2019.

(30) Foreign Application Priority Data

Apr. 24, 2018 (EP) .................................... 18168993
Apr. 24, 2018 (EP) .................................... 18168996

(51) Int. Cl.
| | | |
|---|---|---|
| *A61K 38/00* | (2006.01) | |
| *C07K 14/75* | (2006.01) | |
| *A61P 31/04* | (2006.01) | |
| *A61K 9/00* | (2006.01) | |
| *A61K 45/06* | (2006.01) | |

(52) U.S. Cl.
CPC .............. *C07K 14/75* (2013.01); *A61P 31/04* (2018.01); *A61K 9/0019* (2013.01); *A61K 38/00* (2013.01); *A61K 45/06* (2013.01)

(58) Field of Classification Search
CPC ........ A61K 38/00; A61K 38/36; A61K 45/06; A61K 9/0019; A61P 31/04; C07K 14/75
See application file for complete search history.

(56) References Cited

U.S. PATENT DOCUMENTS

2011/0171285 A1 7/2011 Hook et al.

FOREIGN PATENT DOCUMENTS

| WO | WO 2010/004004 A1 | 1/2010 |
| WO | WO 2010/005513 A2 | 1/2010 |
| WO | WO 2011/083153 A2 | 7/2011 |
| WO | WO 2018/065608 A1 | 4/2018 |

OTHER PUBLICATIONS

WO, PCT/EP2019/060546 ISR and Written Opinion, dated Jul. 16, 2019.
Aaron, D. M., "Overview of Fungal Skin Infections", Merck Manual Consumer Version, downloaded on Jun. 3, 2020 from https://www.merckmanuals.com/home/skin-disorders/fungal-skin-infections/overview-of-fungal-skin-infections, 2 pages.
Bush, L. M., "Overview of Bacteria", Merck Manual Consumer Version, downloaded on Jun. 3, 2020 from https://www.merckmanuals.com/home/infections/bacterial-infections-overview/overview-of-bacteria, 5 pages.
Definition of Infection, NCI Dictionary of Cancer Terms, downloaded on Jun. 3, 2020 from https://www.cancer.gov/publications/dictionaries/cancer-terms/def/infection, 1 page.
Fehrmann, C., et al., "Role for the fibrinogen-binding proteins Coagulase and Efb in *Staphylococcus aureus-Candida* interaction", International Journal of Medical Microbiology, 2013, vol. 303, pp. 230-238.
Flick, M. J., et al., "Genetic elimination of the binding motif on fibrinogen for the *S. aureus* virulence factor ClfA improves host survival in septicemia", Blood, 2013, vol. 121, No. 10, pp. 1783-1794.
Ganesh, V. L., et al., "A Structural Model of the *Staphylococcus aureus* ClfA-Fibrinogen Interaction Opens New Avenues for the Design of Anti-*Staphylococcal* Therapeutics", PLoS Pathogens, 2008, vol. 4, No. 11, pp. 1-10.
Hawiger, J., et al., "Interaction of Human Fibrinogen With *Staphylococci*: Presence of a Binding Region on Normal and Abnormal Fibrinogen Variants and Fibrinogen Derivatives", Blood, 1978, vol. 51, No. 5, pp. 799-812.
Ko, YP, et al., "Fibrinogen Is at the Interface of Host Defense and Pathogen Virulence in *Staphylococcus aureus* Infection", Semin. Thromb. Hemost., 2016, vol. 42, No. 4, pp. 408-421.
Mcdevitt, D., et al., "Characterization of the interaction between the *Staphylococcus aureus* clumping factor (ClfA) and fibrinogen", Eur. J. Biochem., 1997, vol. 247, pp. 416-424.
Opal, S. M., "Non-antibiotic treatments for bacterial diseases in an era of progressive antibiotic resistance", Critical Care, 2016, vol. 20, pp. 397-399.
Revankar, S. G., "Overview of Fungal Infections", Merck Manual Consumer Version, downloaded on Jun. 3, 2020 from https://www.merckmanuals.com/home/infections/fungal-infections/overview-of-fungal-infections, 5 pages.
Uitte De Willige, S., et al., "The pleiotropic role of the fibrinogen γ' chain in hemostasis", Blood, 2009, vol. 114, No. 19, pp. 3994-4001.

*Primary Examiner* — Aradhana Sasan
*Assistant Examiner* — Mercy H Sabila
(74) *Attorney, Agent, or Firm* — One LLP

(57) ABSTRACT

The present invention relates to compositions comprising fibrinogen gamma prime variants for use in the treatment or prevention of an infection and methods of administering the composition. The fibrinogen gamma prime variants in the composition comprise at least one fibrinogen gamma prime polypeptide chain. The compositions for use according to the invention may also comprise other fibrinogen variants. Compositions comprising fibrinogen gamma prime variants according to the invention improve survival time after infection up to more than 200 percent compared to WT fibrinogen. They may be used both therapeutically and prophylactically.

13 Claims, 7 Drawing Sheets

Specification includes a Sequence Listing.

390  NRLTIGEGQQHHLGGAKQAGDV 411

VRPEHPAETEY DSLYPEDDL

390  NRLTIGEGQQHHLGGAKQVRPE      411
412  HPAETEYDSLYPEDDL            427

SEQUENCE LISTING

```
<160> NUMBER OF SEQ ID NOS: 7

<210> SEQ ID NO 1
<211> LENGTH: 22
<212> TYPE: PRT
<213> ORGANISM: human

<400> SEQUENCE: 1

Asn Arg Leu Thr Ile Gly Glu Gly Gln Gln His His Leu Gly Gly Ala
1               5                   10                  15

Lys Gln Ala Gly Asp Val
            20

<210> SEQ ID NO 2
<211> LENGTH: 20
<212> TYPE: PRT
<213> ORGANISM: human

<400> SEQUENCE: 2

Val Arg Pro Glu His Pro Ala Glu Thr Glu Tyr Asp Ser Leu Tyr Pro
1               5                   10                  15

Glu Asp Asp Leu
            20

<210> SEQ ID NO 3
<211> LENGTH: 38
<212> TYPE: PRT
<213> ORGANISM: human

<400> SEQUENCE: 3

Asn Arg Leu Thr Ile Gly Glu Gly Gln Gln His His Leu Gly Gly Ala
1               5                   10                  15

Lys Gln Val Arg Pro Glu His Pro Ala Glu Thr Glu Tyr Asp Ser Leu
            20                  25                  30

Tyr Pro Glu Asp Asp Leu
        35

<210> SEQ ID NO 4
<211> LENGTH: 610
<212> TYPE: PRT
<213> ORGANISM: Homo sapiens
```

<400> SEQUENCE: 4

```
Ala Asp Ser Gly Glu Gly Asp Phe Leu Ala Glu Gly Gly Val Arg
 1               5                  10                  15

Gly Pro Arg Val Val Glu Arg His Gln Ser Ala Cys Lys Asp Ser Asp
            20                  25                  30

Trp Pro Phe Cys Ser Asp Glu Asp Trp Asn Tyr Lys Cys Pro Ser Gly
        35                  40                  45

Cys Arg Met Lys Gly Leu Ile Asp Glu Val Asn Gln Asp Phe Thr Asn
50                  55                  60

Arg Ile Asn Lys Leu Lys Asn Ser Leu Phe Glu Tyr Gln Lys Asn Asn
65                  70                  75                  80

Lys Asp Ser His Ser Leu Thr Thr Asn Ile Met Glu Ile Leu Arg Gly
                85                  90                  95

Asp Phe Ser Ser Ala Asn Asn Arg Asp Asn Thr Tyr Asn Arg Val Ser
            100                 105                 110

Glu Asp Leu Arg Ser Arg Ile Glu Val Leu Lys Arg Lys Val Ile Glu
        115                 120                 125

Lys Val Gln His Ile Gln Leu Leu Gln Lys Asn Val Arg Ala Gln Leu
130                 135                 140

Val Asp Met Lys Arg Leu Glu Val Asp Ile Asp Ile Lys Ile Arg Ser
145                 150                 155                 160

Cys Arg Gly Ser Cys Ser Arg Ala Leu Ala Arg Glu Val Asp Leu Lys
                165                 170                 175

Asp Tyr Glu Asp Gln Gln Lys Gln Leu Glu Gln Val Ile Ala Lys Asp
            180                 185                 190

Leu Leu Pro Ser Arg Asp Arg Gln His Leu Pro Leu Ile Lys Met Lys
        195                 200                 205

Pro Val Pro Asp Leu Val Pro Gly Asn Phe Lys Ser Gln Leu Gln Lys
210                 215                 220

Val Pro Pro Glu Trp Lys Ala Leu Thr Asp Met Pro Gln Met Arg Met
225                 230                 235                 240

Glu Leu Glu Arg Pro Gly Gly Asn Glu Ile Thr Arg Gly Gly Ser Thr
                245                 250                 255

Ser Tyr Gly Thr Gly Ser Glu Thr Glu Ser Pro Arg Asn Pro Ser Ser
            260                 265                 270

Ala Gly Ser Trp Asn Ser Gly Ser Ser Gly Pro Gly Ser Thr Gly Asn
        275                 280                 285

Arg Asn Pro Gly Ser Ser Gly Thr Gly Gly Thr Ala Thr Trp Lys Pro
290                 295                 300

Gly Ser Ser Gly Pro Gly Ser Thr Gly Ser Trp Asn Ser Gly Ser Ser
305                 310                 315                 320

Gly Thr Gly Ser Thr Gly Asn Gln Asn Pro Gly Ser Pro Arg Pro Gly
                325                 330                 335

Ser Thr Gly Thr Trp Asn Pro Gly Ser Ser Glu Arg Gly Ser Ala Gly
            340                 345                 350

His Trp Thr Ser Glu Ser Ser Val Ser Gly Ser Thr Gly Gln Trp His
        355                 360                 365

Ser Glu Ser Gly Ser Phe Arg Pro Asp Ser Pro Gly Ser Gly Asn Ala
370                 375                 380

Arg Pro Asn Asn Pro Asp Trp Gly Thr Phe Glu Glu Val Ser Gly Asn
385                 390                 395                 400

Val Ser Pro Gly Thr Arg Arg Glu Tyr His Thr Glu Lys Leu Val Thr
                405                 410                 415
```

```
Ser Lys Gly Asp Lys Glu Leu Arg Thr Gly Lys Glu Lys Val Thr Ser
            420                 425                 430

Gly Ser Thr Thr Thr Arg Arg Ser Cys Ser Lys Thr Val Thr Lys
        435                 440                 445

Thr Val Ile Gly Pro Asp Gly His Lys Glu Val Thr Lys Glu Val Val
450                 455                 460

Thr Ser Glu Asp Gly Ser Asp Cys Pro Glu Ala Met Asp Leu Gly Thr
465                 470                 475                 480

Leu Ser Gly Ile Gly Thr Leu Asp Gly Phe Arg His Arg His Pro Asp
                485                 490                 495

Glu Ala Ala Phe Phe Asp Thr Ala Ser Thr Gly Lys Thr Phe Pro Gly
                500                 505                 510

Phe Phe Ser Pro Met Leu Gly Glu Phe Val Ser Glu Thr Glu Ser Arg
            515                 520                 525

Gly Ser Glu Ser Gly Ile Phe Thr Asn Thr Lys Glu Ser Ser Ser His
            530                 535                 540

His Pro Gly Ile Ala Glu Phe Pro Ser Arg Gly Lys Ser Ser Ser Tyr
545                 550                 555                 560

Ser Lys Gln Phe Thr Ser Ser Thr Ser Tyr Asn Arg Gly Asp Ser Thr
                565                 570                 575

Phe Glu Ser Lys Ser Tyr Lys Met Ala Asp Glu Ala Gly Ser Glu Ala
                580                 585                 590

Asp His Glu Gly Thr His Ser Thr Lys Arg Gly His Ala Lys Ser Arg
                595                 600                 605

Pro Val
    610

<210> SEQ ID NO 5
<211> LENGTH: 461
<212> TYPE: PRT
<213> ORGANISM: Homo sapiens

<400> SEQUENCE: 5

Gln Gly Val Asn Asp Asn Glu Glu Gly Phe Phe Ser Ala Arg Gly His
1               5                   10                  15

Arg Pro Leu Asp Lys Lys Arg Glu Glu Ala Pro Ser Leu Arg Pro Ala
            20                  25                  30

Pro Pro Pro Ile Ser Gly Gly Gly Tyr Arg Ala Arg Pro Ala Lys Ala
        35                  40                  45

Ala Ala Thr Gln Lys Lys Val Glu Arg Lys Ala Pro Asp Ala Gly Gly
    50                  55                  60

Cys Leu His Ala Asp Pro Asp Leu Gly Val Leu Cys Pro Thr Gly Cys
65                  70                  75                  80

Gln Leu Gln Glu Ala Leu Leu Gln Gln Glu Arg Pro Ile Arg Asn Ser
                85                  90                  95

Val Asp Glu Leu Asn Asn Asn Val Glu Ala Val Ser Gln Thr Ser Ser
            100                 105                 110

Ser Ser Phe Gln Tyr Met Tyr Leu Leu Lys Asp Leu Trp Gln Lys Arg
        115                 120                 125

Gln Lys Gln Val Lys Asp Asn Glu Asn Val Val Asn Glu Tyr Ser Ser
    130                 135                 140

Glu Leu Glu Lys His Gln Leu Tyr Ile Asp Glu Thr Val Asn Ser Asn
145                 150                 155                 160
```

Ile Pro Thr Asn Leu Arg Val Leu Arg Ser Ile Leu Glu Asn Leu Arg
                165                 170                 175

Ser Lys Ile Gln Lys Leu Glu Ser Asp Val Ser Ala Gln Met Glu Tyr
            180                 185                 190

Cys Arg Thr Pro Cys Thr Val Ser Cys Asn Ile Pro Val Val Ser Gly
        195                 200                 205

Lys Glu Cys Glu Glu Ile Ile Arg Lys Gly Gly Glu Thr Ser Glu Met
    210                 215                 220

Tyr Leu Ile Gln Pro Asp Ser Ser Val Lys Pro Tyr Arg Val Tyr Cys
225                 230                 235                 240

Asp Met Asn Thr Glu Asn Gly Gly Trp Thr Val Ile Gln Asn Arg Gln
                245                 250                 255

Asp Gly Ser Val Asp Phe Gly Arg Lys Trp Asp Pro Tyr Lys Gln Gly
            260                 265                 270

Phe Gly Asn Val Ala Thr Asn Thr Asp Gly Lys Asn Tyr Cys Gly Leu
        275                 280                 285

Pro Gly Glu Tyr Trp Leu Gly Asn Asp Lys Ile Ser Gln Leu Thr Arg
    290                 295                 300

Met Gly Pro Thr Glu Leu Leu Ile Glu Met Glu Asp Trp Lys Gly Asp
305                 310                 315                 320

Lys Val Lys Ala His Tyr Gly Gly Phe Thr Val Gln Asn Glu Ala Asn
                325                 330                 335

Lys Tyr Gln Ile Ser Val Asn Lys Tyr Arg Gly Thr Ala Gly Asn Ala
            340                 345                 350

Leu Met Asp Gly Ala Ser Gln Leu Met Gly Glu Asn Arg Thr Met Thr
        355                 360                 365

Ile His Asn Gly Met Phe Phe Ser Thr Tyr Asp Arg Asp Asn Asp Gly
    370                 375                 380

Trp Leu Thr Ser Asp Pro Arg Lys Gln Cys Ser Lys Glu Asp Gly Gly
385                 390                 395                 400

Gly Trp Trp Tyr Asn Arg Cys His Ala Ala Asn Pro Asn Gly Arg Tyr
                405                 410                 415

Tyr Trp Gly Gly Gln Tyr Thr Trp Asp Met Ala Lys His Gly Thr Asp
            420                 425                 430

Asp Gly Val Val Trp Met Asn Trp Lys Gly Ser Trp Tyr Ser Met Arg
        435                 440                 445

Lys Met Ser Met Lys Ile Arg Pro Phe Phe Pro Gln Gln
    450                 455                 460

<210> SEQ ID NO 6
<211> LENGTH: 411
<212> TYPE: PRT
<213> ORGANISM: Homo sapiens

<400> SEQUENCE: 6

Tyr Val Ala Thr Arg Asp Asn Cys Cys Ile Leu Asp Glu Arg Phe Gly
1               5                   10                  15

Ser Tyr Cys Pro Thr Thr Cys Gly Ile Ala Asp Phe Leu Ser Thr Tyr
            20                  25                  30

Gln Thr Lys Val Asp Lys Asp Leu Gln Ser Leu Glu Asp Ile Leu His
        35                  40                  45

Gln Val Glu Asn Lys Thr Ser Glu Val Lys Gln Leu Ile Lys Ala Ile
    50                  55                  60

Gln Leu Thr Tyr Asn Pro Asp Glu Ser Ser Lys Pro Asn Met Ile Asp
 65                  70                  75                  80

Ala Ala Thr Leu Lys Ser Arg Lys Met Leu Glu Glu Ile Met Lys Tyr
                 85                  90                  95

Glu Ala Ser Ile Leu Thr His Asp Ser Ser Ile Arg Tyr Leu Gln Glu
            100                 105                 110

Ile Tyr Asn Ser Asn Asn Gln Lys Ile Val Asn Leu Lys Glu Lys Val
        115                 120                 125

Ala Gln Leu Glu Ala Gln Cys Gln Glu Pro Cys Lys Asp Thr Val Gln
    130                 135                 140

Ile His Asp Ile Thr Gly Lys Asp Cys Gln Asp Ile Ala Asn Lys Gly
145                 150                 155                 160

Ala Lys Gln Ser Gly Leu Tyr Phe Ile Lys Pro Leu Lys Ala Asn Gln
                165                 170                 175

Gln Phe Leu Val Tyr Cys Glu Ile Asp Gly Ser Gly Asn Gly Trp Thr
            180                 185                 190

Val Phe Gln Lys Arg Leu Asp Gly Ser Val Asp Phe Lys Lys Asn Trp
        195                 200                 205

Ile Gln Tyr Lys Glu Gly Phe Gly His Leu Ser Pro Thr Gly Thr Thr
    210                 215                 220

Glu Phe Trp Leu Gly Asn Glu Lys Ile His Leu Ile Ser Thr Gln Ser
225                 230                 235                 240

Ala Ile Pro Tyr Ala Leu Arg Val Glu Leu Glu Asp Trp Asn Gly Arg
                245                 250                 255

Thr Ser Thr Ala Asp Tyr Ala Met Phe Lys Val Gly Pro Glu Ala Asp
            260                 265                 270

Lys Tyr Arg Leu Thr Tyr Ala Tyr Phe Ala Gly Gly Asp Ala Gly Asp
        275                 280                 285

Ala Phe Asp Gly Phe Asp Phe Gly Asp Asp Pro Ser Asp Lys Phe Phe
    290                 295                 300

Thr Ser His Asn Gly Met Gln Phe Ser Thr Trp Asp Asn Asp Asn Asp
305                 310                 315                 320

Lys Phe Glu Gly Asn Cys Ala Glu Gln Asp Gly Ser Gly Trp Trp Met
                325                 330                 335

Asn Lys Cys His Ala Gly His Leu Asn Gly Val Tyr Tyr Gln Gly Gly
            340                 345                 350

Thr Tyr Ser Lys Ala Ser Thr Pro Asn Gly Tyr Asp Asn Gly Ile Ile
        355                 360                 365

Trp Ala Thr Trp Lys Thr Arg Trp Tyr Ser Met Lys Lys Thr Thr Met
    370                 375                 380

Lys Ile Ile Pro Phe Asn Arg Leu Thr Ile Gly Glu Gly Gln Gln His
385                 390                 395                 400

His Leu Gly Gly Ala Lys Gln Ala Gly Asp Val
                405                 410

<210> SEQ ID NO 7
<211> LENGTH: 427
<212> TYPE: PRT
<213> ORGANISM: Homo sapiens

<400> SEQUENCE: 7

Tyr Val Ala Thr Arg Asp Asn Cys Cys Ile Leu Asp Glu Arg Phe Gly
1               5                   10                  15

```
Ser Tyr Cys Pro Thr Thr Cys Gly Ile Ala Asp Phe Leu Ser Thr Tyr
             20                  25                  30

Gln Thr Lys Val Asp Lys Asp Leu Gln Ser Leu Glu Asp Ile Leu His
             35                  40                  45

Gln Val Glu Asn Lys Thr Ser Glu Val Lys Gln Leu Ile Lys Ala Ile
 50                  55                  60

Gln Leu Thr Tyr Asn Pro Asp Glu Ser Ser Lys Pro Asn Met Ile Asp
 65                  70                  75                  80

Ala Ala Thr Leu Lys Ser Arg Lys Met Leu Glu Ile Met Lys Tyr
                 85                  90                  95

Glu Ala Ser Ile Leu Thr His Asp Ser Ser Ile Arg Tyr Leu Gln Glu
                100                 105                 110

Ile Tyr Asn Ser Asn Asn Gln Lys Ile Val Asn Leu Lys Glu Lys Val
                115                 120                 125

Ala Gln Leu Glu Ala Gln Cys Gln Glu Pro Cys Lys Asp Thr Val Gln
130                 135                 140

Ile His Asp Ile Thr Gly Lys Asp Cys Gln Asp Ile Ala Asn Lys Gly
145                 150                 155                 160

Ala Lys Gln Ser Gly Leu Tyr Phe Ile Lys Pro Leu Lys Ala Asn Gln
                165                 170                 175

Gln Phe Leu Val Tyr Cys Glu Ile Asp Gly Ser Gly Asn Gly Trp Thr
                180                 185                 190

Val Phe Gln Lys Arg Leu Asp Gly Ser Val Asp Phe Lys Lys Asn Trp
                195                 200                 205

Ile Gln Tyr Lys Glu Gly Phe Gly His Leu Ser Pro Thr Gly Thr Thr
                210                 215                 220

Glu Phe Trp Leu Gly Asn Glu Lys Ile His Leu Ile Ser Thr Gln Ser
225                 230                 235                 240

Ala Ile Pro Tyr Ala Leu Arg Val Glu Leu Glu Asp Trp Asn Gly Arg
                245                 250                 255

Thr Ser Thr Ala Asp Tyr Ala Met Phe Lys Val Gly Pro Glu Ala Asp
                260                 265                 270

Lys Tyr Arg Leu Thr Tyr Ala Tyr Phe Ala Gly Gly Asp Ala Gly Asp
                275                 280                 285

Ala Phe Asp Gly Phe Asp Phe Gly Asp Asp Pro Ser Asp Lys Phe Phe
                290                 295                 300

Thr Ser His Asn Gly Met Gln Phe Ser Thr Trp Asp Asn Asp Asn Asp
305                 310                 315                 320

Lys Phe Glu Gly Asn Cys Ala Glu Gln Asp Gly Ser Gly Trp Trp Met
                325                 330                 335

Asn Lys Cys His Ala Gly His Leu Asn Gly Val Tyr Tyr Gln Gly Gly
                340                 345                 350

Thr Tyr Ser Lys Ala Ser Thr Pro Asn Gly Tyr Asp Asn Gly Ile Ile
                355                 360                 365

Trp Ala Thr Trp Lys Thr Arg Trp Tyr Ser Met Lys Lys Thr Thr Met
                370                 375                 380

Lys Ile Ile Pro Phe Asn Arg Leu Thr Ile Gly Glu Gly Gln Gln His
385                 390                 395                 400

His Leu Gly Gly Ala Lys Gln Val Arg Pro Glu His Pro Ala Glu Thr
                405                 410                 415

Glu Tyr Asp Ser Leu Tyr Pro Glu Asp Asp Leu
                420                 425
```

THERAPEUTIC USES OF FIBRINOGEN GAMMA PRIME VARIANTS

CROSS-REFERENCE TO RELATED APPLICATIONS

The subject application is a continuation of U.S. application Ser. No. 16/716,172, filed Dec. 16, 2019, which is a continuation of PCT Patent Application No. PCT/EP2019/060546, filed Apr. 24, 2019, which claims priority to European Patent Application No. 18168996.9, filed on Apr. 24, 2018, and European Patent Application No. 18168993.6, filed on Apr. 24, 2018, all of which are incorporated by reference herein in their entirety for all purposes.

TECHNICAL FIELD

The present invention generally relates to the use of fibrinogen variants comprising a gamma prime chain, in particular to their use to prevent or treat infections.

BACKGROUND OF THE INVENTION

Fibrinogen is a soluble plasma glycoprotein and a dimeric molecule, consisting of two pairs of three polypeptide chains designated Aα, Bβ and γ, which are connected by disulfide bridges. The three polypeptide chains are encoded by three separate genes and synthesized individually from 3 mRNAs. Assembly of the three polypeptide chains (Aα, Bβ, and γ) into its final form as a six-chain dimer (Aα, Bβ, γ) 2 occurs in the lumen of the endoplasmic reticulum (ER). The mature, dominant form of human fibrinogen in circulation consists of Aα chains that are 610 amino acids in length, Bβ chains of 461 amino acids and γ chains of 411 amino acids and is referred to as normal fibrinogen, HMW fibrinogen, wild type (WT) fibrinogen.

However, it has been demonstrated that circulating fibrinogen is a highly heterogeneous mixture of several variants that occur in blood of all healthy individuals and are the result of an alteration in either the Aα chains or Bβ chains or γ chains.

A well-known variant of fibrinogen, which is the result of alternative splicing, is the plasma fibrinogen gamma prime (pFib γ') variant. The pFib γ' variant represents about 10-15% of the total fibrinogen in human plasma. In circulation, pFib γ' is present as a heterodimer in which one half of the dimeric fibrinogen molecule contains the gamma chain as found in WT fibrinogen, and the other half of the same fibrinogen molecule contains a variant gamma chain. In humans, the variant gamma chain in pFib γ' consists of 427 amino acids (γ427) rather than 411 amino acids (γ411) as found in WT fibrinogen. In the γ427 chain the four carboxyl-terminal amino acids Ala-Gly-Asp-Val (AGDV) of the γ411 chain are replaced by a 20-mer peptide.

Beyond playing a key role in controlling haemorrhage, fibrinogen can serve as an early line of defence for host protection by limiting pathogen growth and mediating host defence mechanisms against pathogens. However, several pathogens have evolved ways to interact with host fibrinogen in order to enhance pathogen virulence. For example, *S. aureus* uses bacterial cell wall-anchored clumping factor A (ClfA) to bind to fibrinogen that, supposedly because of its dimeric structure, induces fibrinogen-dependent clumping of *S. aureus* in suspension. The ClfA binding site in fibrinogen is mapped to the carboxyl-terminus of the fibrinogen γ411 of WT fibrinogen. The binding and subsequent clumping of the bacteria, via ClfA and fibrinogen, is considered an important virulence factor of bacteria and in several studies the effect of preventing the binding of ClfA to fibrinogen gamma chains has been studied. U.S. Publ. No. 2011/0171285 discloses in vitro studies with mammalian fibrinogens to which ClfA cannot bind because in both gamma chains the glutamine (Q) before the carboxyl-terminal AGDV sequence has been modified. Flick et al. (2013) Blood (121): 1783-1794 discloses homozygous transgenic mice in which the QAGDV sequence in the carboxyl-terminal end of their fibrinogen gamma chains has been deleted (Fib γ$^{\Delta 5/\Delta 5}$ mice). These mutant mice have a significantly increased survival as compared to mice with WT fibrinogen when challenged with *S. aureus* bacteria.

However, these studies use molecules which would be equivalent to homodimer pFib γ', which has never been isolated from plasma. It is not likely that sufficient amounts of this fibrinogen variant for medical use may be obtained from plasma. In addition, the effect of the modified fibrinogen in Fib γ$^{\Delta 5/\Delta 5}$ mice on bacterial binding, clumping and virulence is established without the presence of any WT fibrinogen and therefore does not demonstrate that this approach would be useful as a therapeutic or prophylactic product that is able to compete with the normal WT fibrinogen of the host and still introduce a clinically meaningful effect in the presence of WT fibrinogen.

Accordingly, it would be desirable to find alternative fibrinogen compositions which are readily available, have an effect on bacterial virulence in the presence of host WT fibrinogen and, therefore, are clinically meaningful.

DETAILED DESCRIPTION OF THE INVENTION

Figures 1, 2, 3, 4:
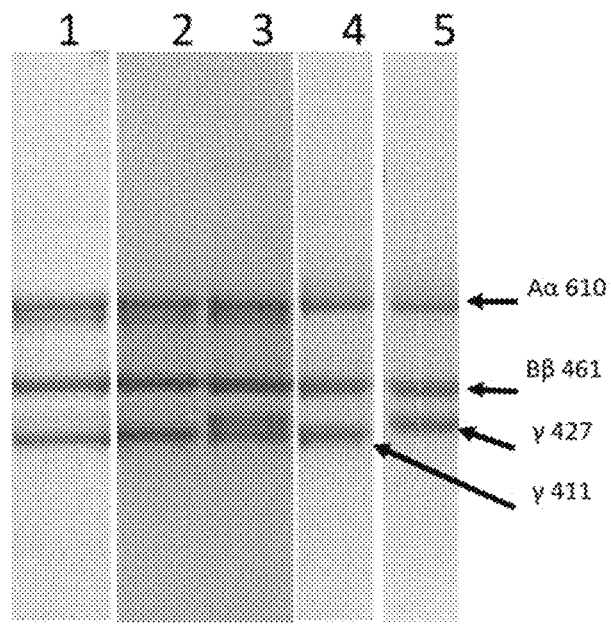
FIG. 1 Carboxyl-terminus of human WT fibrinogen gamma chain (γ411), according to SEQ ID NO. 1. The Gln-Ala-Gly-Asp-Val (QAGDV) motif at positons 407-411 is underlined.
FIG. 2 The 20-mer peptide, according to SEQ ID NO. 2, which substitutes AGDV in the gamma chain of human fibrinogen gamma prime.
FIG. 3 Carboxyl-terminus of the human gamma prime chain (γ427), according to SEQ ID NO. 3.
FIG. 4 SDS-PAGE analysis of purified fibrinogen preparations from plasma, lane 1: pFib Total, lane 2: pFib γ411/γ411 and lane 3: pFib γ427/γ411 and recombinant fibrinogens, lane 4: rhFib γ411/γ411 and lane 5 rhFib γ427/γ427.

The present invention relates to a composition comprising a fibrinogen gamma prime variant for use in the treatment or prevention of an infection. Fibrinogen gamma prime variants have two alpha polypeptide chains, two beta polypeptide chains and two gamma polypeptide chains, wherein at least one of the gamma polypeptide chains comprises a carboxyl-terminal sequence according to SEQ ID NO. 3.

In the context of the present invention, the carboxyl-terminus of a fibrinogen gamma chain refers to amino acid positions 390-411 of the gamma chain of WT fibrinogen. The position of a particular amino acid within a gamma chain may be determined by alignment with the amino acid sequence of the WT fibrinogen gamma chain (SEQ ID NO. 6). All or part of the gamma chain sequence, in particular its carboxyl-terminus, may be aligned. A standard sequence alignment tool, such as for example the Smith-Waterman algorithm, may be used for alignment. Sequences are said to be aligned when the alignment score is highest, when aligned with this sequence.

In the context of the present invention, the term wild type (WT) fibrinogen refers to the mature, dominant form of human fibrinogen in circulation consisting of Aa chains that are 610 amino acids in length, Bβ chains of 461 amino acids and γ chains of 411 amino acids. The carboxyl-terminus of the WT fibrinogen gamma chain is according to SEQ ID NO. 1 and also depicted in FIG. 1.

Substitution of AGDV in the carboxyl-terminus of the WT fibrinogen gamma chain (SEQ ID NO. 1) by VRPEHPAETEYDSLYPEDDL (SEQ ID NO. 2 and FIG. 2) leads to a gamma chain according to SEQ ID NO. 3, also referred to as a gamma prime polypeptide chain. As used herein, amino acid abbreviations are according to IUPAC nomenclature, therefore, QAGDV refers to Gln-Ala-Gly-Asp-Val and VRPEHPAETEYDSLYPEDDL refers to Val-Arg-Pro-Glu-His-Pro-Ala-Glu-Thr-Glu-Tyr-Asp-Ser-Leu-Tyr-Pro-Glu-Asp-Asp-Leu.

In humans, this gamma prime polypeptide chain has 427 amino acids. If a fibrinogen molecule comprises one WT gamma polypeptide chain (γ411) and one gamma prime polypeptide chain (γ427), this variant is referred to here as fibrinogen gamma prime heterodimer or Fib γ427/411. If both gamma polypeptide chains are of the gamma prime type (γ427), this variant is referred to as fibrinogen gamma prime homodimer or Fib γ427/427. The compositions for use according to the invention may comprise or consist of mixtures of these gamma prime variants, such as a mixture of fibrinogen gamma prime heterodimer and homodimer, or it may comprise or consist of one type of gamma prime variant.

The applicants have surprisingly found that compositions comprising a fibrinogen gamma prime variant have several advantages in comparison to WT fibrinogen and in comparison to fibrinogen mutants so far suggested for treatment of infection. Compositions comprising a fibrinogen gamma prime variant give a significant improvement in survival when used for treating or preventing infection in a subject, in particular when administered by injection or infusion. In contrast to WT fibrinogen, the fibrinogen gamma prime variants reduce virulence of bacterial infections in animal models, despite some of these variants behaving similar to WT fibrinogen in in vitro bacterial adhesion and clumping experiments. Another advantage is that compositions comprising fibrinogen gamma prime seem to have an effect on infection which is independent of reduced bacterial binding to fibrinogen. Another advantage is that compositions comprising fibrinogen gamma prime are effective both in prophylactic treatment and in therapeutic treatment. Another advantage is that some embodiments of these fibrinogen gamma prime variants are present in plasma in sufficiently high amounts to be isolated from plasma. Yet another advantage is that these fibrinogen gamma prime variants have an effect on bacterial virulence in the presence of host WT fibrinogen. Yet another advantage is that the effect on survival of these fibrinogen gamma prime variants is independent of severity of the infection or the bacterial load. Therefore, they are clinically meaningful.

The invention shows that compositions for use according to the invention are effective in the treatment or prevention of infection in animal models, although the fibrinogen gamma prime variants or compositions comprising them may behave like WT fibrinogen in in vitro binding or clumping experiments. Binding or clumping may be determined by measuring absorbance at 570 nm, for example as described by Flick et al. (2013) Blood (121): 1783-1794.

Infection refers to the invasion or multiplication of microorganisms, such as bacteria and fungi, which are not normally present within an individual's body or which are present in abnormal amounts. Such infectious microorganisms are here also referred to as pathogens. An infection may be subclinical, without symptoms, or it may be clinically, with apparent symptoms. The effect of treatment or prevention may be permanent or temporary, such as for several days, several weeks, several months or several years. It may be complete or partial. Partial effective prevention includes prevention of invasion or multiplication of some microorganisms, and not others. Partial effective treatment includes reduction of invasion or multiplication of some microorganisms which are present in abnormal amounts, for example a reduction by 5% to 100% or 5% to 60% or 60% to 100%. Preferably, prevention or treatment is complete and permanent. In one embodiment, compositions for use according to the invention are used in the treatment or prevention of a fibrinogen-binding pathogen in a human subject, in particular those binding to the carboxyl-terminus of the gamma chain.

The composition for use according to the invention may comprise from 0.05% w/w to 20% w/w of fibrinogen by weight of the composition, such as from 0.1% w/w to 10% w/w or 0.5% to 15% w/w of fibrinogen by weight of the composition and optionally a pharmaceutically-acceptable carrier or vehicle, such as diluents, lubricants, binders, colourants, antioxidants, surfactants, preservatives, antioxidants, solvents, suspending agents, wetting agents or surfactants. A "pharmaceutically acceptable excipient", "pharmaceutically acceptable diluent", "pharmaceutically acceptable carrier" or "pharmaceutically acceptable adjuvant" means an excipient, diluent, carrier or adjuvant that are useful in preparing a pharmaceutical composition that are generally safe, non-toxic and neither biologically nor otherwise undesirable. These materials should does not adversely affect the stability of the composition or any component thereof.

If the fibrinogen gamma prime is the only fibrinogen variant in the composition, the composition for use according to the invention may comprise from 0.05% w/w to 20% w/w of the fibrinogen gamma prime variant by weight of the composition, such as from 0.1% w/w to 10% w/w or 0.5% to 15% w/w of the fibrinogen gamma prime variant by weight of the composition.

Alternatively, the composition for use according to the invention may comprise other fibrinogen variants in addition to the gamma prime variants, such as fibrinogen with two gamma polypeptide chains comprising a carboxyl-terminal sequence according to SEQ ID NO. 1. In that case, the total fibrinogen content of the composition is from 0.05% w/w to 20% w/w, such as from 0.1% w/w to 10% w/w or 0.5% to 15% w/w by weight of the composition and the fibrinogen gamma prime variant content is at least 25% w/w of the total fibrinogen in the composition. In one embodiment, a composition for use according to the invention comprises a combination of homodimer or heterodimer fibrinogen gamma prime and WT fibrinogen. Therefore, in one embodiment of the invention there is provided a composition for use in the treatment or prevention of an infection, the composition comprising:

(i) a fibrinogen gamma prime variant having two alpha polypeptide chains, two beta polypeptide chains and two gamma polypeptide chains, wherein at least one of the gamma polypeptide chain comprises a carboxyl-terminal sequence according to SEQ ID NO. 3.

(ii) not more than about 75% WT fibrinogen by weight of the total fibrinogen in the composition.

Accordingly, said composition may comprise not more than about 5%, 10%, 20%, 50% or about 60% or about 1% to 25%, 25% to 50%, 25% to 70% or 50% to 70% of WT fibrinogen, by weight of the total fibrinogen in the composition, whereby the total fibrinogen content of the composition is preferably from 0.05% w/w to 20% w/w, such as from 0.1% w/w to 10% w/w or 0.5% to 15% w/w, by weight of the composition and the fibrinogen gamma prime variant content is at least 25% w/w of the total fibrinogen in the composition.

The fibrinogen in the composition for use according to the invention may be obtained by methods known in the art. For example, it may be obtained by isolation from plasma, preferably mammalian plasma or from plasma fibrinogen total mixture. Plasma fibrinogen, typically comprising a mixture of fibrinogen variants, may be commercially obtained, for example from Enzyme Research Labs, Swansea, United Kingdom as FIB 3, or may be isolated form a mammalian, preferably human, individual. The plasma may be derived from one individual or may be pooled from more individuals. A suitable method for isolation from plasma may comprise precipitation or chromatography, in particular anion exchange, for example as described by Lawrence et al. Blood 1993, vol 82, pp 2406-2413.

Alternatively, the fibrinogen in the composition may be obtained by recombinant production, for example by cloning or chemical synthesis of the encoding genomic or cDNA followed by transfection using a host cell or cell culture system, such as a mammalian or human cell culture system. Recombinant production of proteins has many advantages over the use of plasma derived materials. These include its preferred safety profile, the possibility to make variants in a pure way and there is an unlimited supply. However, in order to produce it in an economically feasible way, high expression levels of intact, functional fibrinogen or its variants are required. In addition, for specific applications, proper post-translational modifications (e.g. glycosylation) are required. Therefore, in a further embodiment of the invention, for pharmaceutical standards, the fibrinogen variant is produced in a mammalian cell culture system, such as in baby hamster kidney (BHK) cells, NSO cells, Sp2/0 cells, PER.C6 cells, HEK293 cells, insect cell, Chinese Hamster Ovary (CHO) cells or African Green Monkey derived COS cells. In a preferred embodiment, the mammalian fibrinogen in the composition for use according to the invention is produced in CHO cells.

Recombinant production of fibrinogen comprised in compositions for use according to the invention typically involves transfection of a mammalian host cell, preferably a CHO cell, with a vector comprising a nucleotide sequence encoding an alpha polypeptide chain, a vector comprising a nucleotide sequence encoding a beta polypeptide chain and vectors comprising nucleotide sequences encoding the desired gamma prime polypeptide chains.

In one embodiment, the composition comprises mixtures of recombinantly produced and plasma-derived fibrinogen gamma prime molecules. These mixtures may comprise one type of fibrinogen gamma prime variant or several fibrinogen gamma prime variants. Of course, recombinantly produced and plasma-derived fibrinogen gamma prime may be mutated, or modified after production or isolation to obtain a variant with desired properties, e.g. to enhance activity, protein half-life, protein stability, protein localization and protein efficacy, as long as the fibrinogen gamma prime molecules provided for use according to the invention have retained the normal functions of a fibrinogen gamma prime molecule.

In one embodiment, the fibrinogen gamma prime in the composition for use according to the invention is fibrinogen gamma prime as found in plasma (pFib γ'), optionally produced recombinantly, in its homodimeric or heterodimeric form.

Several common single amino acid substitution polymorphisms are known that do not alter any known function of the fibrinogen gamma prime molecule. Such polymorphism or alterations may be present in the gamma chain outside the carboxyl-terminus. Post-translational modifications, proteolytic degradation and alternative splicing may be present in one or both of the alpha or beta chains of the fibrinogen gamma prime molecule. For example, the fibrinogen gamma prime molecule in the composition for use according to the invention may comprise a variant alpha chain which has arisen through genetic polymorphisms, differences in glycosylation or phosphorylation, (partial) proteolysis of its carboxyl-terminal part or alternative splicing. In some cases, this may lead to fibrinogen variants with differences in function (e.g. fibrin polymerization, platelet binding, proteolytic degradation). Preferably, it does not alter thrombin binding, clot-forming activity or Factor XIIIa-mediated cross-linking in fibrinogen gamma prime molecules for use according to the invention.

The composition for use according to the invention is used for treatment or prevention of an infection. The infection is typically caused by or associated with the invasion or multiplication of microorganisms, such as bacteria and fungi, which are not normally present within an individual's body or which are present in abnormal amounts. Such infectious microorganisms are here also referred to as pathogens. In one embodiment, the infection is caused by or associated with Gram negative bacteria or Gram positive bacteria, such as *Escherichia, Bacteroides, Salmonella, Yersinia, Neisseria, Pseudomonas, Staphylococcus, Enterococcus, Streptococcus, Clostridium, Listeria, Bacillus*, in particular *Staphylococcus aureus*, including vancomycin resistant *S. aureus*, methicillin-resistant *S. aureus* and multi-resistant *S. aureus* strains, including *S. aureus* USA 300 WT and *S. aureus* Newman. In another embodiment, the infection is caused by or associated with fungi, such as *Aspergillus* or *Candida*. The pathogens may be fibrinogen binding, in particular, binding to the carboxyl-terminus of the fibrinogen gamma chain, more in particular to the AGDV site of the fibrinogen gamma polypeptide chain.

The composition for use according to the invention may advantageously be used for treatment or prevention of any infection, such as pneumonia; sepsis; bacteremia; peritonitis; endocarditis; skin or soft tissue infection; osteoarticular infections; prosthetic joint infection; bone infection; pleuropulmonary infection; wound infection; epidural abscesses; meningitis; toxic shock syndrome; urinary tract infection or septic thrombophlebitis.

The composition may further comprise one or more antimicrobials, including antibiotics, such as penicillin, amoxicillin, ampicillin, cephalosporins and tetracyclines, and antifungal agents.

The composition for use according to the invention may be administered by various routes, preferably systemically, be it enterally or parenterally. Preferably, it is administered by injection or infusion. In one embodiment, it is administered parenterally, for example by injection, such as by intravenous, intra-arterial, intraperitoneal, intraglandular or intravesicular injection or infusion. The terms "administration" or "administering" as used herein may include the process in which the compositions, alone or in combination with other fibrinogen variants or compositions, are delivered to a human or animal subject.

The dosing of the compositions to obtain a therapeutic or prophylactic effect may be determined by the circumstances of the subject, as known in the art and may be accomplished through individual or unit doses of the compositions or by a combined or pre-packaged or pre-formulated dose of a composition. Administration may depend upon the amount of composition administered, the number of doses, and duration of treatment. For example, multiple doses may be administered. The duration of administration of the composition, e.g., the period of time over which the composition is administered, may vary, depending on any of a variety of factors, including subject response. The amount of the composition administered may vary according to factors such as the degree of susceptibility of the individual and the age, sex and weight of the individual.

The composition for use according to the present invention may be administered to a vertebrate "individual", "patient" or "subject", preferably a mammal, more preferably a human. Mammals also include, but are not limited to, farm animals, sport animals and pets. For veterinary applications, suitable subjects may include, for example, livestock such as cattle, sheep, goats, cows, swine; poultry such as chickens, ducks, geese and turkeys; and domesticated animals particularly pets such as dogs, rabbits, mice and cats. Other animals suitable for administration of a fibrinogen gamma prime composition disclosed herein include horse, mule, donkey, deer, alpaca, llama, bison, buffalo, boar and yak.

In one embodiment, the present invention relates to a composition for use in the treatment or prevention of an infection in a human individual, the composition comprising a variant fibrinogen consisting of two Aα chains according to SEQ ID NO. 4, two Bβ chains according to SEQ ID NO. 5 and two gamma polypeptide chains, wherein at least one of the gamma polypeptide chains comprises a carboxyl-terminal sequence according to SEQ ID NO. 3.

In one embodiment, the present invention relates to a composition for use in the treatment or prevention of an infection in a human individual, the composition comprising a variant fibrinogen consisting of two Aα chains as found in WT fibrinogen or according to SEQ ID NO. 4, two Bβ chains as found in WT fibrinogen or according to SEQ ID NO. 5 and two gamma polypeptide chains, wherein at least one of the gamma polypeptide chains is as found in plasma fibrinogen gamma prime or according to SEQ ID NO. 7.

In another embodiment, the present invention relates to a composition for use in the treatment or prevention of an infection in a human individual, the composition comprising a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3 and wherein the fibrinogen in the composition is produced recombinantly, optionally wherein said recombinant fibrinogen is human.

In another embodiment of the invention there is provided a composition for use in the treatment or prevention of an infection, comprising a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3, wherein the infection is caused by or associated with a fibrinogen-binding pathogen in a human or animal subject, in particular those binding to the carboxyl-terminus of the gamma chain.

In yet another embodiment of the invention, there is provided a composition for use in the treatment or prevention of an infection, comprising a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3, wherein the infection is caused by or associated with a fibrinogen-binding pathogen, in particular binding to the carboxyl-terminus of the gamma chain in a human or animal subject, selected from Gram negative bacteria, Gram positive bacteria or fungi, and combinations thereof. The pathogen may be selected from the group consisting of the genera *Escherichia, Bacteroides, Salmonella, Yersinia, Neisseria, Pseudomonas, Staphylococcus, Enterococcus, Streptococcus, Clostridium, Listeria, Bacillus; Aspergillus* or *Candida* and is preferably an *S. aureus*, including vancomycin resistant *S. aureus*, methicillin-resistant *S. aureus* and multi-resistant *S. aureus* strains. The infection may be selected from one or more of: pneumonia e.g. hospital-acquired pneumonia; sepsis; bacteremia; peritonitis; endocarditis;

skin or soft tissue infection e.g. impetigo; osteoarticular infections e.g. osteomyelitis, septic arthritis; prosthetic joint infection; bone infection; pleuropulmonary infections; wound infection e.g. diabetic ulcers; epidural abscesses; meningitis; toxic shock syndrome; urinary tract infection or septic thrombophlebitis.

In a further embodiment of the invention there is provided a composition for use in the treatment or prevention of an infection, comprising a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3, and further comprising a pharmaceutically acceptable carrier, for the treatment, prevention or reduction of infection or virulence of a fibrinogen-binding pathogen in a human or animal subject, selected from Gram negative bacteria, Gram positive bacteria, fungi, or combinations thereof, or for the treatment, prevention or reduction of a symptom in a subject caused by or associated with a fibrinogen-binding pathogen, wherein said prevention or reduction of a symptom, and/or virulence results in prolongation of host survival and/or sensitisation to antimicrobial therapy, including antibiotics and antifungal agents.

In a further embodiment of the invention there is provided a composition for use in the treatment or prevention of an infection, comprising a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3, and further comprising a pharmaceutically acceptable carrier, for the treatment, prevention or reduction of infection or virulence of a fibrinogen-binding pathogen in a human or animal subject, selected from Gram negative bacteria, Gram positive bacteria, fungi or combinations thereof. Accordingly, said pathogen may be a Gram-negative bacteria, such as *Escherichia coli, Bacteroides fragilis, Salmonella* spp, *Yersinia* spp, *Neisseria meningitides*, or *Pseudomonas aeruginosa*; a Gram-positive bacteria such as from the genera Staphylococci, Enterococci, Streptococci, *Clostridium, Listeria*, or *Bacilli*; or a fungus such as *Aspergillus* or *Candida*.

In a further embodiment of the invention there is provided a composition for use in the treatment or prevention of an infection, comprising a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3, said composition further comprising one or more antimicrobial agents, such as antibiotics or antifungal agents.

In a further embodiment of the invention there is provided a composition for use in the treatment or prevention of an infection, consisting of a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3. The fibrinogen variant may have two alpha polypeptide chains according to SEQ ID NO. 4 and two beta polypeptide chains according to SEQ ID NO. 5.

In yet another embodiment of the invention there is provided a composition for use in the treatment or prevention of an infection, consisting of a variant fibrinogen having two alpha polypeptide chains, two beta polypeptide chains and two gamma polypeptide chains, wherein one of the gamma polypeptide chains comprises a carboxyl-terminus according to SEQ ID NO. 1 and the other gamma polypeptide chain comprises an amino acid sequence according to SEQ ID NO. 3.

In yet another embodiment of the invention there is provided a composition for use in the treatment or prevention of an infection, consisting of a variant fibrinogen having two alpha polypeptide chains, two beta polypeptide chains and two gamma polypeptide chains, wherein both gamma polypeptide chains comprise a carboxyl-terminus according to SEQ ID NO. 3, also depicted in FIG. 3.

In another embodiment of the invention there is provided a composition for use in the treatment or prevention of an infection, comprising a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3, wherein the fibrinogen in the composition is produced recombinantly, optionally wherein said recombinant fibrinogen is mammalian.

In a further embodiment of the invention there is provided a composition for use in the treatment or prevention of an infection, comprising a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3, said composition further comprising one or more antimicrobial agents selected from but not limited to: penicillin G, oxacillin, vancomycin, flucloxacillin, amoxicillin, ampicillin, cloxacillin antipseudomonal penicillins, methicillin, nafcillin, dicloxacillin, cephalosporins, carbapenems, imipenem, meropenem, ertapenem, doripenem, tetracyclines, macrolides, fluoroquinolones, trimethoprim/sulfamethoxazole (TMP/SMX), gentamicin, vancomycin, daptomycin, telavancin, cefazolin, mupirocin, teicoplanin, tetracyclines, minocycline, doxycycline, erythromycin, rifampin, clindamycin, linezolid, aminoglycosides and antifungal agents.

In a further embodiment, the Gram positive bacteria is selected from *S. afermentans, S. aureus*, MRSA, *S. auricularis, S. capitis, S. caprae, S. cohnii, S. epidermidis, S. felis, S. haemolyticus, S. hominis, S. intermedius, S. lugdunensis, S. pettenkoferi, S. saprophyticus, S. schleiferi, S. simulans, S. vitulus, S. warneri*, and *S. xylosus* and streptococcal species including *Streptococcus agalactiae* (Group B *Streptococcus*) and *Streptococcus pyogenes* (Group A *Streptococcus*).

In a further embodiment of the invention, the Gram positive bacterium is an *S. aureus*, such as vancomycin resistant *S. aureus*, methicillin-resistant *S. aureus* or multi-resistant *S. aureus* strains, such as BD-635, ST250 MRSA-1, ST2470-MRSA-I, ST239-MRSA-III, ST5-MRSA-II, ST5-MRSA-IV, ST239-MRSA-III, EMRSA15, EMRSA 16, MRSA252, ST5:USA100, EMRSA 1, ST8:USA300, ST1 USA400, ST8:USA500, ST59:USA1000, USA1100, USA600, USA800, USA300, ST30, ST93, ST80, ST59, CC22, CC8, CC425, and CC398.

In another embodiment of the invention, the fibrinogen composition according to the invention is for administration by injection or infusion, in particular by intravenous, intra-arterial, intraperitoneal, intraglandular or intravesicular injection or infusion, optionally further comprising a pharmaceutically-acceptable carrier.

In another embodiment of the invention, the fibrinogen composition according to the invention is a pharmaceutical composition or preparation, preferably sterile.

In a further embodiment of the invention the fibrinogen composition according to the invention, is administered simultaneously, separately or sequentially with one or more antimicrobial agents, including antibiotics, and may be selected from but not limited to: penicillin G, oxacillin, vancomycin, flucloxacillin, amoxicillin, ampicillin, antipseudomonal penicillins, methicillin, nafcillin, cloxacillin, dicloxacillin, vancomycin, cephalosporins, carbapenems, imipenem, meropenem, ertapenem, doripenem, tetracyclines, macrolides, fluoroquinolones, trimethoprim/sulfamethoxazole, cefazolin, (TMP/SMX), gentamicin, daptomycin, telavancin, mupirocin, teicoplanin, tetracyclines, minocycline, doxycycline, erythromycin, rifampin, clindamycin, linezolid, aminoglycosides and antifungal agents.

In a further embodiment of the invention there is provided a method of treating, delaying or preventing onset, and/or reducing or controlling the severity of fibrinogen-binding pathogen-associated infection in a human or animal subject, comprising the steps of administering a fibrinogen composition as disclosed herein, to a human or animal subject, to treat, delay or prevent onset and/or to treat, reduce or control the severity of fibrinogen-binding pathogen-associated clinical symptoms, optionally wherein said pathogen is selected from: Gram negative bacteria, Gram positive bacteria, fungi, or combinations thereof.

In a further embodiment of the invention there is provided a method of treating or preventing fibrinogen-binding pathogenic load in the bloodstream or heart in a human or animal subject, for example as associated with endocarditis, comprising the steps of administering a fibrinogen composition according to the invention disclosed herein, to a human or animal subject, to reduce said fibrinogen-binding pathogen load in the bloodstream or heart, optionally before surgery in a patient at risk of said endocarditis.

In a further embodiment of the invention there is provided the use of a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3, in the preparation of a medicament for the treatment, prevention or reduction of infection or virulence of a fibrinogen-binding pathogen in a human or animal subject.

In yet a further embodiment of the invention there is provided a use of a variant fibrinogen having two alpha polypeptide chains, two beta polypeptide chains and two gamma polypeptide chains, wherein at least one of the gamma polypeptide chains comprises a carboxyl-terminal sequence according to SEQ ID NO. 3, in the preparation of a medicament for the treatment, prevention or reduction of a symptom in a subject caused by or associated with a fibrinogen-binding pathogen, such as: pneumonia e.g. hospital-acquired pneumonia; sepsis; bacteremia; peritonitis; endocarditis; skin or soft tissue infection e.g. impetigo; osteoarticular infections e.g. osteomyelitis, septic arthritis; prosthetic joint infection; bone infection; pleuropulmonary infections; wound infection e.g. diabetic ulcers; epidural abscesses; meningitis; toxic shock syndrome; urinary tract infection or septic thrombophlebitis, or combinations thereof.

In a further embodiment of the invention there is provided a use of a variant fibrinogen having two alpha polypeptide chains, two beta polypeptide chains and two gamma polypeptide chains, wherein at least one of the gamma polypeptide chains comprises a sequence according to SEQ ID NO. 3, in the preparation of a medicament for the treatment, prevention or reduction of infection or virulence of a fibrinogen-binding pathogen in a human or animal subject, wherein said fibrinogen is human fibrinogen.

The fibrinogen composition according to the invention may include a "therapeutically effective amount" or a "prophylactically effective amount" of the variant fibrinogen or composition according to the invention. A "therapeutically effective amount" refers to an amount effective, at dosages and for periods of time necessary, to achieve the desired therapeutic result. A therapeutically effective amount of a variant fibrinogen or compositions thereof may be determined by a person skilled in the art and may vary according to factors such as the disease state, age, sex, and weight of the individual, and the ability of the mammalian fibrinogen or composition to elicit a desired response in the individual. A therapeutically effective amount is also one in which any toxic or detrimental effects of variant fibrinogens or compositions of the invention are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A therapeutically effective amount of a variant fibrinogen composition of the present disclosure, may be about 2.0 mg/kg to about 800 mg/kg, about 3.0 mg/kg to about 700 mg/kg, about 5 mg/kg to about 650 mg/kg, about 10 mg/kg to about 600 mg/kg, about 45 mg/kg to about 550 mg/kg, about 60 mg/kg to about 400 mg/kg, about 65 mg/kg to about 350 mg/kg, about 75 mg/kg to about 250 mg/kg, about 80 mg/kg to about 200 mg/kg, about 85 mg/kg to about 150 mg/kg, and about 90 mg/kg to about 100 mg/kg, relative to the dose of variant fibrinogen per kg of subject body weight.

In a further embodiment of the invention, the fibrinogen composition according to the invention is administered once or at multiple times occurring within a period of about 2, 3, 6, 12 or 24 hours. In some methods, the fibrinogen is administered multiple times at intervals of about 2, 3, 4, 5, 6, 7, or more days.

In a further embodiment of the invention, the fibrinogen variant according to the invention demonstrates an in vivo half-life of about 6, 12, 24, 36, 48 or 72 hours or more.

Some examples of materials which can serve as pharmaceutically acceptable carriers include buffering agents such as, but not limited to, magnesium hydroxide and aluminum hydroxide; alginic acid; pyrogen-free water; isotonic saline; Ringer's solution; ethyl alcohol, and phosphate buffer solutions, as well as other nontoxic excipients such as, but not limited to, sodium lauryl sulphate and magnesium stearate, as well as, preservatives and antioxidants which can also be present in the composition, according to the judgment of the formulator. Techniques and formulations may generally be found in "Remington's Pharmaceutical Sciences," (Meade Publishing Co., Easton, Pa.). Pharmaceutically-acceptable vehicles or carriers for systemic administration according to the invention may include at least one of diluents, lubricants, binders, colourants, antioxidants, surfactants, preservatives, antioxidants, solvents, suspending agents, wetting agents, surfactants, combinations thereof, and others. Preferably the carrier, vehicle or diluent includes sterile water for injection, sterile isotonic saline, sterile Ringer's solution or sterile lactate solution, the selection of which would be well known to those skilled in the art. Suitable solvents include water, isotonic saline, ethyl oleate, glycerine, hydroxylated castor oils, alcohols such as ethanol, and phosphate buffer solutions. The amount of solvent(s) in a systemic composition may range from 80% to about 99.95% w/w or w/v. These materials should does not adversely affect the stability of the composition or any component thereof.

Although the amounts of components in the systemic compositions may vary depending on the type of systemic composition prepared, in general, systemic compositions include from 0.05% w/w to 20% w/w, such as from 0.1% w/w to 10% w/w or 0.5% to 15% w/w of fibrinogen and 80% to 99.95% w/w or w/v of one or more pharmaceutically-acceptable carriers. Compositions for parenteral administration may include from 0.05% w/w to 20% w/w, such as from 0.1% w/w to 10% w/w or 0.5% to 15% w/w of fibrinogen and 90% to 99.9% w/w or w/v of a pharmaceutically-acceptable carrier including a diluent and/or a solvent.

The compositions for use according to the invention are typically sterile and stable under the conditions of manufacture and storage. The composition may be in a variety of forms, suitable for systemic administration. Preferably, the composition is suitable for injection and for example formulated for parenteral administration via a route selected from intravenous, intra-arterial, intraperitoneal, intraglandular or intravesicular injection or infusion. In this context, intraglandular includes direct administration to the lumen of glands such as the udders of mammalian animals, particularly livestock such as cows, sheep and pigs. Other animals suitable for administration of a fibrinogen composition disclosed herein include sheep, cow, goat, pig, horse, mule, donkey, deer, dog, cat, rabbit, mouse, alpaca, llama, bison, buffalo, boar and yak. Typically, not human fibrinogen, but the animal equivalent of fibrinogen would be used. In this way, mastitis in dairy cattle, in particular cow may be prevented or treated.

In a first aspect, the invention relates to a composition for use in the treatment or prevention of an infection, the composition comprising or consisting of a variant fibrinogen having two alpha polypeptide chains, two beta polypeptide chains and two gamma polypeptide chains, wherein at least one of the gamma polypeptide chains comprises a sequence according to SEQ ID NO. 3.

In a second aspect, the invention relates to a composition for use according to the first aspect, wherein one of the gamma polypeptide chains comprises a sequence according to SEQ ID NO. 1 and the other gamma polypeptide chain comprises a sequence according to SEQ ID NO. 3.

In a third aspect, the invention relates to a composition for use according to the first or second aspect, wherein the two alpha polypeptide chains are according to SEQ ID NO. 4 and the two beta polypeptide chains are according to SEQ ID NO. 5.

In a fourth aspect, the invention relates to a composition for use according to the first to third aspect, wherein at least one of the gamma polypeptide chains is according to SEQ ID NO. 7.

In a fifth aspect, the invention relates to a composition for use according to any of the previous aspects, further comprising not more than about 75% of a fibrinogen comprising two alpha, two beta and two gamma polypeptide chains, wherein both gamma polypeptide chains carboxyl-termini are according to SEQ ID NO. 1 and wherein the 75% is by weight of the total fibrinogen in the composition.

In a sixth aspect, the invention relates to a composition for use according to any of the previous aspects, wherein the fibrinogen in the composition is recombinant or plasma-derived or mixtures thereof.

In a seventh aspect, the invention relates to a composition for use according to any of the previous aspects, wherein the infection in a human or animal subject is caused by or associated with a pathogen binding to the carboxyl-terminus of the fibrinogen gamma chain.

In an eighth aspect, the invention relates to a composition for use according to any of the previous aspects, wherein the infection is caused by one or more pathogens selected from the group consisting of Gram negative bacteria, Gram positive bacteria and fungi.

In a ninth aspect, the invention relates to a composition for use according to any of the previous aspects, wherein the pathogen is a *Staphylococcus aureus*, including vancomycin resistant *S. aureus*, methicillin-resistant *S. aureus* and multi-resistant *S. aureus* strains.

In a tenth aspect, the invention relates to a composition for use according to any of the previous aspects, wherein the infection is selected from one or more of: pneumonia; sepsis; bacteremia; peritonitis; endocarditis; skin or soft tissue infection; osteoarticular infections; prosthetic joint infection; bone infection; pleuropulmonary infection; wound infection; epidural abscesses; meningitis; toxic shock syndrome; urinary tract infection or septic thrombophlebitis.

In an eleventh aspect, the invention relates to a composition for use according to any of the previous aspects, wherein the composition is for administration by injection or infusion, preferably for administration by intravenous, intra-arterial, intraperitoneal, intraglandular or intravesicular injection or infusion.

In a twelfth aspect, the invention relates to a composition for use according to any of the previous aspects, wherein the composition further comprises a pharmaceutically-acceptable carrier or adjuvant.

I Any numerical range recited herein includes all values from the lower value to the upper value and all possible combinations of numerical values between and including the lowest value and the highest value enumerated are to be considered to be expressly stated in this application.

As used herein, "treat", "treatment", "treating", and the like refer to acting upon a condition with an agent to affect the condition by improving or altering it. The condition includes, but is not limited to infection, such as those caused by bacteria. The agent includes, but is not limited to, fibrinogen variants or compositions capable of inhibiting or preventing infection, such as those caused by bacteria. For example, the agent may include the fibrinogen gamma prime variant or compositions described herein. The improvement or alteration may include an improvement in symptoms or an alteration in the physiologic pathways associated with the condition. The aforementioned terms cover one or more treatments of a condition in a subject (e.g., a mammal, typically a human or non-human animal of veterinary interest), and include: (a) reducing the risk of occurrence of the condition in a subject determined to be predisposed to the condition but not yet diagnosed, (b) impeding the development of the condition, (c) reduction of the condition/infection, and/or virulence and/or clinical manifestations, (d) delaying or preventing onset of the condition/infection, (e) to treat, reduce or control the severity of the condition, and/or (f) relieving the condition, e.g., causing regression of the condition and/or relieving one or more condition symptoms (e.g., reducing or eliminating the infection).

As used herein the terms "reducing", "suppressing", "inhibiting", "decreasing", "removing" or the like in reference to microorganisms means complete or partial inhibition (more than 50%, preferably more than 90%, still more preferably more than 95% or even more than 99%) of microorganisms (in the term of number of remaining cells or remaining total biomass). Further, inhibition may be permanent or temporary. In terms of temporary inhibition, microorganisms may be inhibited for a time sufficient to produce the desired effect (for instance at least 5 days, preferably at least 10 days or more). Preferably, the inhibition of microorganisms is complete and/or permanent (no persisters) ("eradicating" or "eradication").

As used herein, "preventing" or the like in reference to microorganisms means complete or partial prevention (more than 50%, preferably more than 90%, still more preferably more than 95% or even more than 99%) of microorganisms (in the term of number of remaining cells or remaining total biomass) and also includes within its scope processes associated with microorganisms. Further, prevention may be permanent or temporary. In terms of temporary prevention, microorganisms may be inhibited for a time sufficient to produce the desired effect (for instance at least 5 days, preferably at least 10 days or more). Preferably, the prevention of microorganisms is complete and/or permanent.

"Wound" as used herein refers to any damage to any tissue of a patient which results in the loss of blood from the circulatory system or any other fluid from the patient's body. The damage may have been caused by any agent or source, including traumatic injury, infection or surgical intervention. A wound may be in a soft tissue, such as an organ, or in hard tissue, such as bone. The tissue may be an internal tissue, such as an organ or blood vessel, or an external tissue, such as the skin. The loss of blood may be internal, such as from a ruptured organ, or external, such as from a laceration.

The skilled person will understand that the above embodiments may be combined to form new embodiments within the scope of the invention.

Having now generally described the invention, the same will be more readily understood through reference to the following examples which are provided by way of illustration, and are not intended to be limiting of the present invention, unless specified.

EXAMPLES

Example 1 Isolation of Fibrinogen Variants from Plasma

Total plasma fibrinogen mixture (pFib total) comprising wild type (WT) fibrinogen (pFib γ411/411) and fibrinogen gamma prime (pFibγ427/411) was obtained from Enzyme Research Labs, Swansea, United Kingdom (FIB 3). This was used as starting material to separate the plasma fibrinogen with two WT gamma polypeptide chains (pFib γ411/411) from the plasma fibrinogen variant with one gamma prime polypeptide chain and one WT gamma polypeptide chain (pFib γ427/411) using anion exchange chromatography as described in Lawrence et al. (Blood 1993, vol 82, no 8, pp 2406-2413). pFib total, pFib γ411/411 and pFib γ427/411 were analysed on SDS-PAGE (Example 3) and used in further experiments as described below.

Mouse fibrinogen from WT mice (mFib γWT/WT) and from homozygous delta5 transgenic mice (mFib γ Δ5/Δ5) was isolated as described by Flick et al. (2013) Blood (121): 1783-1794.

Example 2 Recombinant Production of WT Fibrinogen and Homodimer Fibrinogen Gamma Prime cDNA sequences encoding the fibrinogen Aα610 chain (Alpha wild type, SEQ ID NO. 4), Bβ chain (SEQ ID NO. 5), γ411 (gamma) chain (SEQ ID NO. 6) and γ427 (gamma prime) chain (SEQ ID NO. 7) were cloned in the pCDNA3.1 plasmid (Invitrogen, Carlsbad, Calif., USA) to construct expression vectors for the different fibrinogen chains. Combinations of expression plasmids containing cDNA's encoding Aα, Bβ and γ chains were used to produce fully assembled recombinant human WT fibrinogen (rhFib γ411/411) and recombinant fibrinogen gamma prime homodimer (rhFib γ427/427) by transient expression in HEK 293 cells (Life technologies EXPI293 system) according to the manufacturer's instructions. These recombinant fibrinogen variants were purified using affinity purification on a GPRP column as described in Kuyas C et al. (Thrombosis Haemostasis 1990 Jun. 28; 63 (3): 439-444) and analysed on SDS-PAGE (as described in Example 3)

Example 3 SDS-PAGE Analysis of Fibrinogen Isolated from Plasma and Recombinantly Produced Fibrinogen pFib γ411/411 and pFib γ427/411 isolated from total plasma fibrinogen (pFib total) were subjected to SDS-PAGE analysis under reducing conditions. About 0.5 to 1.0 microgram of the fibrinogen samples was loaded on the SDS-PAGE gel, run for 1 hour at 200 Volt and stained with Coomassie blue stain. The result is shown in FIG. 4.

Lane 1: pFib total (total plasma fibrinogen) showed as dominant bands the Aα 610, Bβ 461 and γ411. A slightly degraded Act band is seen just below the Aα610 band and a faint band at the γ427 position is present. Lane 2: pFib γ411/411 only contains only the γ411 band at the gamma polypeptide position. Lane 3: pFib γ427/411 isolated from pFib total contains wild type Aα610 and Bβ461 polypeptides, but the γ chain polypeptide consists of approximately equal amounts of γ411 and γ427, demonstrating that pFib γ427/411 is a heterodimer with respect to the gamma polypeptide.

For the recombinant products, rhFib γ411/411 and rhFib γ427/427 prepared in Example 2 the results are shown in Lane 4: rhFib γ411/411, containing polypeptide chains Aα610, Bβ461 and γ411. Lane 5: rhFib γ427/427 containing Aα610, Bβ461 and γ427. The polypeptide chains of the recombinantly produced variants correspond to the cDNA sequences used in the transfections.

Example 4 Binding of S. aureus USA 300 WT to Immobilized Compositions of Different Fibrinogen Species The binding experiments were performed as described in Flick (2013) (Blood (121): 1783-1794). Briefly, serial dilutions of the different fibrinogen species were immobilized to 96 well microtiter plates at concentrations ranging from 0 to 25 microgram/ml. Suspensions having an optical density at 600 nm of about 0.4 of S. aureus USA 300 WT and USA 300 ClfA—strains in exponential or stationary growth were added to microtiter plates with immobilized fibrinogen and incubated for 2 hours at 37° C. Non-binding bacteria were removed and adherent bacteria were fixed with 25% formaldehyde solution and stained with 0.1% w/v crystal violet solution. The bound crystal violet was dissolved in 10% v/v acetic and absorbance was measured at 570 nm. The absorbance at 570 nm was plotted against the fibrinogen concentration in the fibrinogen coating solution. Each sample was measured in triplicate.

Figure 5A:
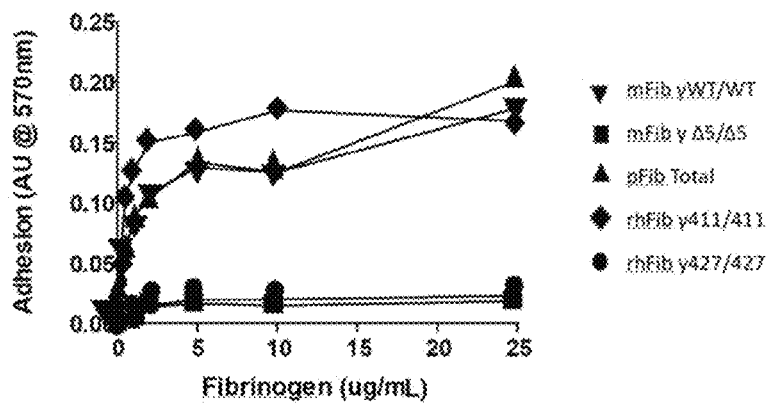
FIG. 5A Adhesion of *S. aureus* USA 300 wild type (WT) to immobilized fibrinogen isolated from mice, human plasma and recombinant fibrinogen.

FIG. 5A demonstrates that exponentially growing S. aureus USA 300 WT do not bind to fibrinogen species in which the QAGDV motif is completely deleted (mFib γ Δ5/Δ5) or wherein the AGDV sequence has been replaced by SEQ ID NO. 2 (rhFib γ427/427). S. aureus USA 300 WT in the stationary growth phase shows a similar binding profile as compared to exponentially growing bacteria (data not shown). USA 300 ClfA-strain did not show any binding to any of the fibrinogen species tested (data not shown). These data show that mFib γ Δ5/Δ5 and rhFib γ427/427 demonstrate similar in vitro binding properties for S. aureus USA 300 WT.

Figure 5B:
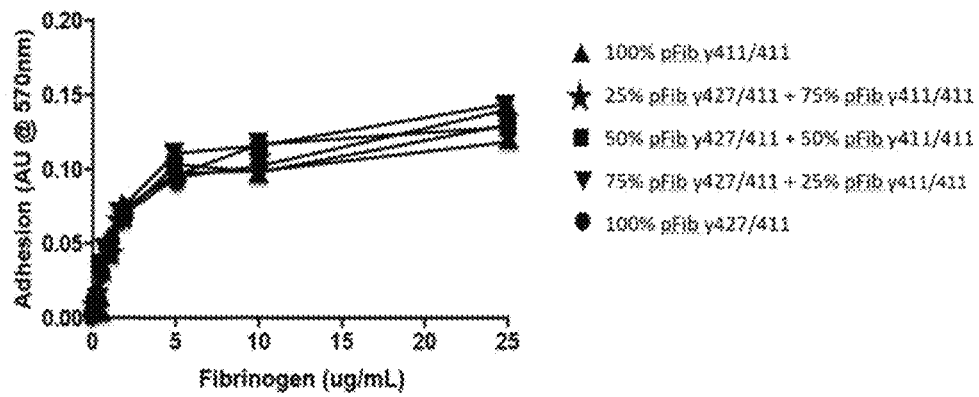
FIG. 5B shows adhesion of *S. aureus* USA 300 wild type (WT) to immobilized WT fibrinogen (pFibγ411/411), fibrinogen gamma prime heterodimer (pFibγ427/411) and various mixtures thereof.

FIG. 5B shows that, surprisingly, the binding profile of exponentially growing S. aureus USA 300 WT to pFib γ427/411 and pFib γ411/411 are virtually identical. The binding profile of pFib γ427/411 which contains approximately equal amount of the gamma polypeptide γ411 and γ427 does not show any significant difference with that of pFib γ411/411, which only contains γ411 polypeptides. Also, the binding profile of the mixtures of pFib γ427/411 and pFib γ411/411 are very similar to the binding profile of 100% pFib γ411/411.

S. aureus bacteria in the stationary growth phase showed similar results (data not shown)

Figure 5C:
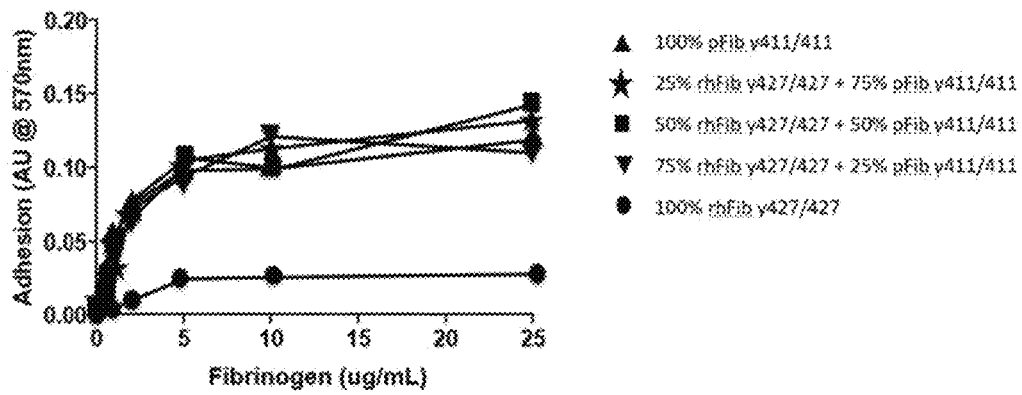
FIG. 5C shows adhesion of *S. aureus* USA 300 wild type (WT) to immobilized WT fibrinogen (pFibγ411/411), fibrinogen gamma prime homodimer (rhFib γ427/427) and various mixtures thereof.

FIG. 5C shows that, surprisingly, the binding profile of exponentially growing S. aureus USA 300 WT of PFib γ411/411 is not influenced by the presence of up to 75% of rhFib γ427/427 in the immobilized fibrinogen composition.

The data in FIGS. 5B and 5C indicate that only complete lack of the QAGDV binding motif or complete replacement of the AGDV motif in the fibrinogen gamma chain leads to reduced ClfA mediated binding of S. aureus to immobilized fibrinogen.

Example 5 Clumping of S. aureus Induced and Supported by Various Compositions Comprising Different Fibrinogen Species Fibrinogen-dependent clumping of exponentially and stationary growing S. aureus USA 300 WT and USA 300 ClfA-strains was performed essentially as described by Flick et al. (Blood (121): 1783-1794; 2013). In brief, serial dilutions of the different purified fibrinogen variants and mixtures thereof were mixed with suspensions of S. aureus in 96 well microtiter plates. The decrease in absorbance at 570 nm was measured and the 1/absorbance 570 nm was plotted versus the fibrinogen concentration as a measure for the amount of clumping.

Figure 6A:
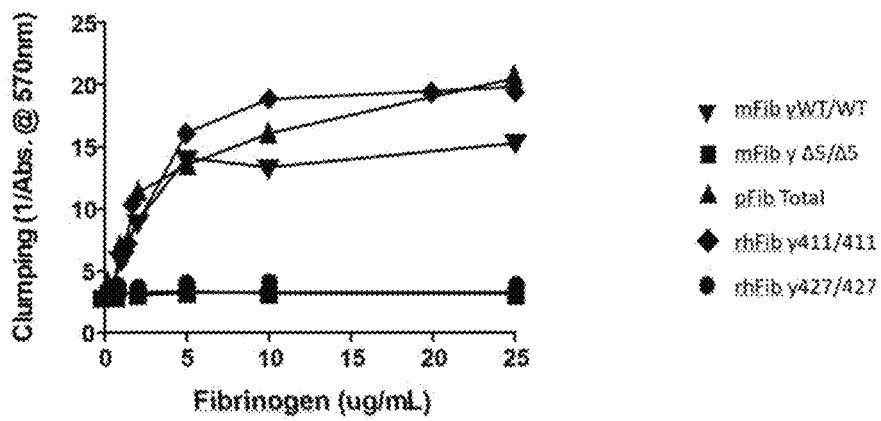
FIG. 6A Clumping of *S. aureus* USA 300 WT induced by fibrinogen isolated from mice, human plasma and recombinant fibrinogen.

FIG. 6A demonstrates that clumping of exponentially growing S. aureus USA 300 WT is not supported by fibrinogen species in which the QAGDV motif is completely deleted (mFib γ Δ5/Δ5) or wherein the AGDV sequence has been replaced by SEQ ID NO. 2 (rhFib γ427/427). S. aureus USA 300 WT in the stationary growth phase shows a similar profile as compared to exponentially growing bacteria (data not shown). USA 300 ClfA-strain did not show clumping with any of the fibrinogen species tested (data not shown). These data show that mFib γ Δ5/Δ5 and rhFib γ427/427 both in a similar way demonstrate complete absence of in vitro clumping properties for S. aureus USA 300 WT.

Figure 6B:
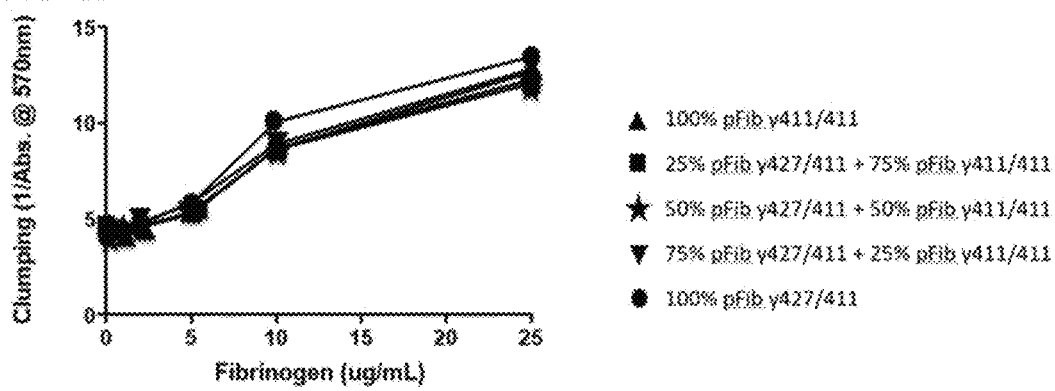
FIG. 6B shows clumping of *S. aureus* USA 300 WT induced by WT fibrinogen (pFibγ411/411), fibrinogen gamma prime heterodimer (pFibγ427/411) and various mixtures thereof.

FIG. 6B shows very surprisingly, that pFibγ427/411 supports clumping of exponentially growing S. aureus bacteria. The clumping curve is virtually identical to the curve of pFib γ411/411. The clumping curve remained similar for mixtures of pFibγ427/411 and pFib γ411/41. No inhibition by pFib γ427/411 on the pFib γ411/411-supported clumping was observed. S. aureus bacteria in a stationary growth phase showed similar results (data not shown).

Figure 6C:
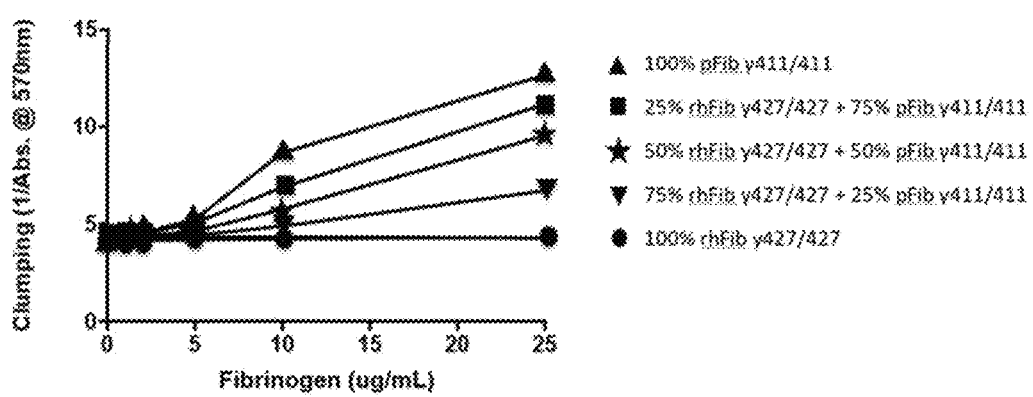
FIGS. 6C and 6D show clumping of *S. aureus* USA 300 WT induced by WT fibrinogen (pFibγ411/411), fibrinogen gamma prime homodimer (rhFibγ427/427) and various mixtures thereof, exponentially growing cells and cells in stationary phase, resp.
Figure 6D:
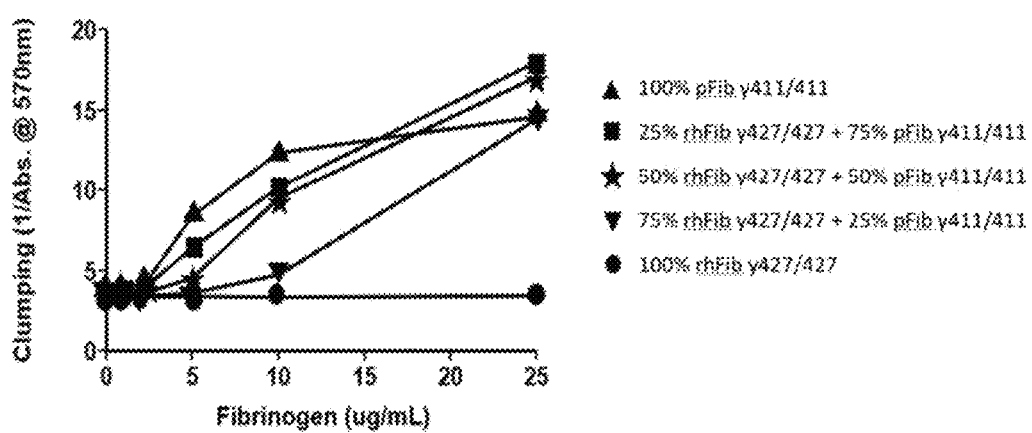

FIGS. 6C and 6D shows that 100% rhFib γ427/427 did not support clumping of exponentially growing S. aureus bacteria. However, using exponentially growing S. aureus bacteria (FIG. 6C), the mixtures of rhFib γ427/427 with pFib γ411/411, at low fibrinogen concentrations, showed a dose dependent inhibition of the pFib γ411/411 induced clumping despite the finding (FIG. 5C) that binding to pFib γ411/411 was not affected by the presence of rhFib γ427/427 in the mixtures. FIG. 6D shows that when using S. aureus in the stationary growth phase the inhibition of clumping by mixtures of rhFib γ427/427 with pFib γ411/411 only occurs at low fibrinogen concentrations and only in the mixture which contains 75% rhFib γ427/427. Complete inhibition of clumping in these experiments was also only observed with 100% rhFib γ427/427.

Clumping experiments using the S. aureus USA 300 ClfA negative strain (data not shown) demonstrated complete absence of clumping with any of the fibrinogen species used, indicating that S. aureus clumping is fully dependent on ClfA mediated interactions with fibrinogen.

The in vitro results from Example 4 demonstrate that ClfA mediated binding (adhesion) of S. aureus to fibrinogen, which is considered an important in vivo virulence factor, is only reduced if 100% of the binding sites in the carboxyl terminus of fibrinogen are lacking (100% rhFib γ427/427 in FIGS. 5B and 5C). No reduced binding is observed when the heterodimer pFibγ 427/411, containing 50% of the gamma carboxyl-terminal binding sites for ClfA (FIG. 5A) or mixtures of rhFib γ427/427 and pFib γ411/411 were used.

Furthermore, the in vitro results from Example 5 demonstrate that ClfA mediated clumping of S. aureus is supported by the heterodimer pFib γ427/411 to the same extent as pFib γ411/411. Mixtures of rhFibγ427/427 and pFib γ411/411 do show a dose dependent decrease of clumping in S. aureus USA 300 WT but only at low fibrinogen concentrations. Complete inhibition of clumping with both exponentially and stationary growing S. aureus is only observed if 100% of the fibrinogen used was rhFib γ427/427 that fully lacks the ClfA binding motif in the carboxyl terminal region of the gamma chain.

Therefore, these in vitro results suggest that a clinically meaning full effect, of reducing the fibrinogen gamma chain ClfA binding motif in a human or animal host infected with S. aureus, is only to be expected if this fibrinogen binding motif is completely absent. No clinical effect is expected of a partial reduction in fibrinogen gamma chains containing the ClfA binding motif.

Figure 7A:
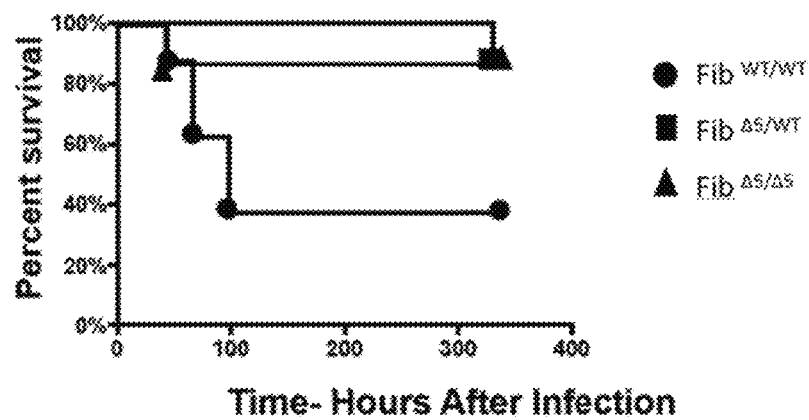
FIG. 7A Survival profiles of fibrinogen WT mice (Fib γ$^{WT/WT}$) heterozygous (Fib γ$^{WT/\Delta 5}$) and homozygous (Fib $\gamma^{\Delta5/\Delta5}$) transgenic fibrinogen delta 5 mice challenged with 2.0×10⁸ CFU.
Figure 7B:
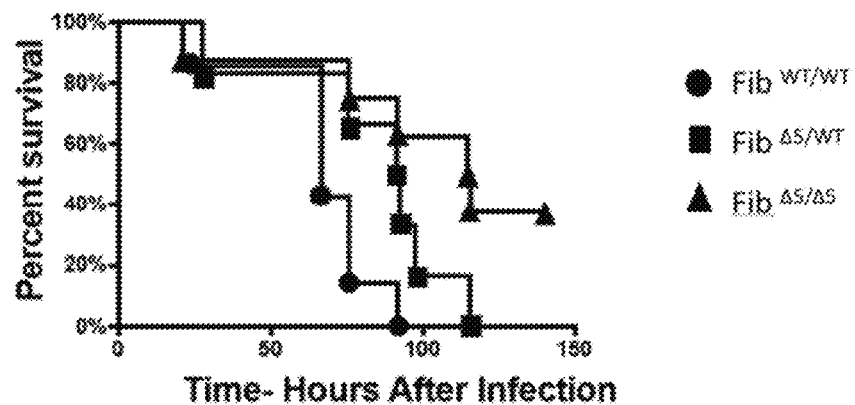
FIG. 7B shows survival profiles of fibrinogen WT mice (Fib $\gamma^{WT/WT}$) heterozygous (Fib $\gamma^{WT/\Delta5}$) and homozygous (Fib $\gamma^{\Delta5/\Delta5}$) transgenic fibrinogen delta 5 mice challenged with 6.0×10⁸ CFU.
Figure 7C:
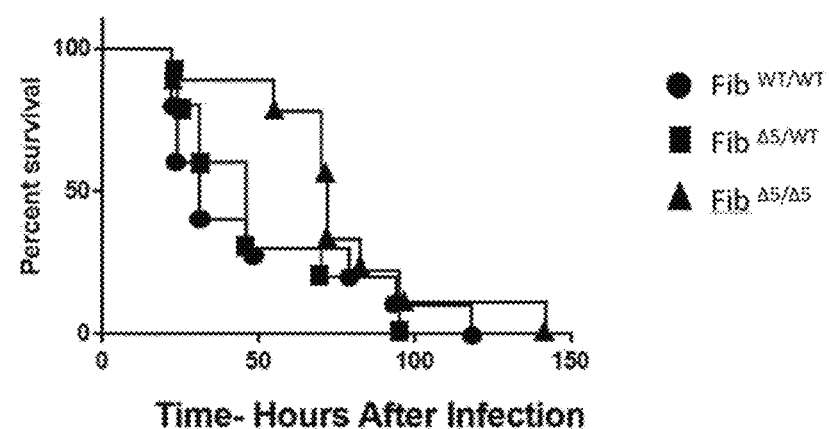
FIG. 7C shows survival profiles of fibrinogen WT mice (Fib $\gamma^{WT/WT}$) heterozygous (Fib $\gamma^{WT/\Delta5}$) and homozygous (Fib $\gamma^{\Delta5/\Delta5}$) transgenic fibrinogen delta 5 mice challenged with 7.0×10⁸ CFU *S. aureus* USA 300 WT.

Example 6 Survival Profiles of Homozygous (Fib $\gamma^{\Delta5/\Delta5}$) and Heterozygous (Fib $\gamma^{WT/\Delta5}$) Delta 5 Mice after Different Challenges of S. aureus USA 300 WT Survival of heterozygous (Fib $\gamma^{WT/\Delta5}$) and homozygous (Fib $\gamma^{\Delta5/\Delta5}$) fibrinogen delta 5 mice (with the QAGDV motif deleted in one or both of the gamma chains), and WT mice were compared after tail vein injection with $2.0\times20^8$ CFU S. aureus USA 300 WT (FIG. 7A) and $6.0\times10^8$ CFU S. aureus USA 300 WT (FIG. 7B) and with $7.0\times10^8$ CFU S. aureus USA 300 WT (FIG. 7C). As expected from the in vitro data in examples 4 and 5 the homozygous delta 5 mice (Fib $\gamma^{\Delta5/\Delta5}$) demonstrated a substantial survival advantage as compared to WT mice at all different challenges with S. aureus. This is also in accordance with the result published by Flick et al. (2013) (Blood (121): 1783-1794). Surprisingly the heterozygous delta 5 mice (Fib $\gamma^{WT/\Delta5}$) lacking only 50% of the fibrinogen gamma chain ClfA binding motif, also demonstrated a significant survival advantage as compared to fibrinogen WT mice. However, the survival advantage in the Fib $\gamma^{WT/\Delta5}$ was strongly dependent on the dose of S. aureus injected. At low dose the effect on survival of the Fib $\gamma^{WT/\Delta5}$ mutation is similar to that of the Fib $\gamma^{\Delta5/\Delta5}$ mice (FIG. 7A) at medium dose it is smaller than for Fib $\gamma^{\Delta5/\Delta5}$ mice (FIG. 7B) and at high dose no survival advantage of Fib $\gamma^{WT/\Delta5}$ was observed any more (FIG. 7C).

These results surprisingly indicate that, despite the in vitro results in example 4 and 5, the presence of fibrinogen lacking the ClfA binding motif in the gamma chain at levels of 50% of the level of the WT fibrinogen (containing the ClfA binding motif) could still provide a meaning full clinical effect on S. aureus virulence. However, the protective effect of the deletion of the QAGDV motif in the Fib $\gamma^{WT/\Delta5}$ mice seems to reduce with increasing severity of the S. aureus infection.

Example 7 Survival Profiles of Fibrinogen Deficient (Fib$^{-/-}$) Mice Prophylactically Treated with pFib Total, pFibγ427/411 Heterodimer and Human pFib γ411/411 after Challenge S. aureus USA 300 WT Fibrinogen deficient mice (Fib-/-) on a C57Black/6J background, generated as described in Suh et al. (Genes & Development. 1995 Aug. 15; 9 (16): 2010-2033), age and gender matched, between 8-12 weeks, were administered pFib γ411/411 or human pFibγ427/411 or pFib Total via tail vein injection. All treatment groups consisted of at least 9 animals. After injection with various fibrinogen species or PBS as control, the animals were challenged with 5×10$^8$ CFU (FIG. 8A) or 1.0×10$^9$ CFU (FIG. 8B) S. aureus USA 300 WT.

Figure 8A:
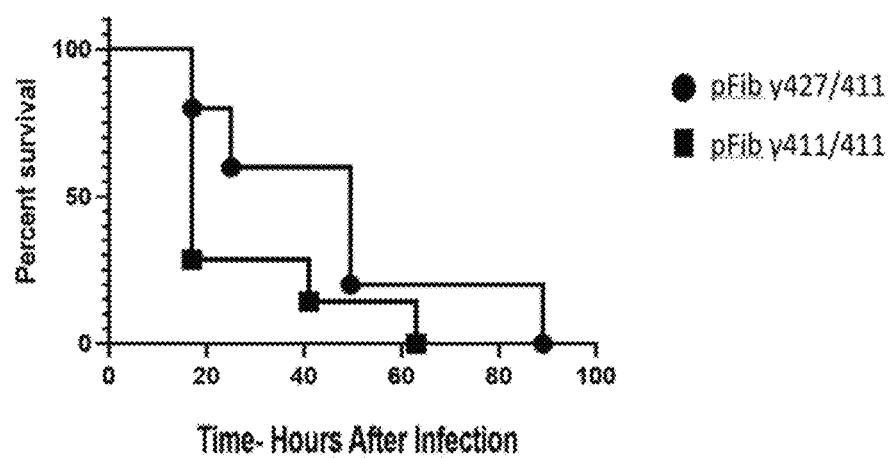
FIG. 8A Survival profiles of fibrinogen deficient mice (Fib⁻/⁻) supplemented with a single dose of different human fibrinogen species from plasma before a challenge with 5.0×10⁸ CFU.
Figure 8B:
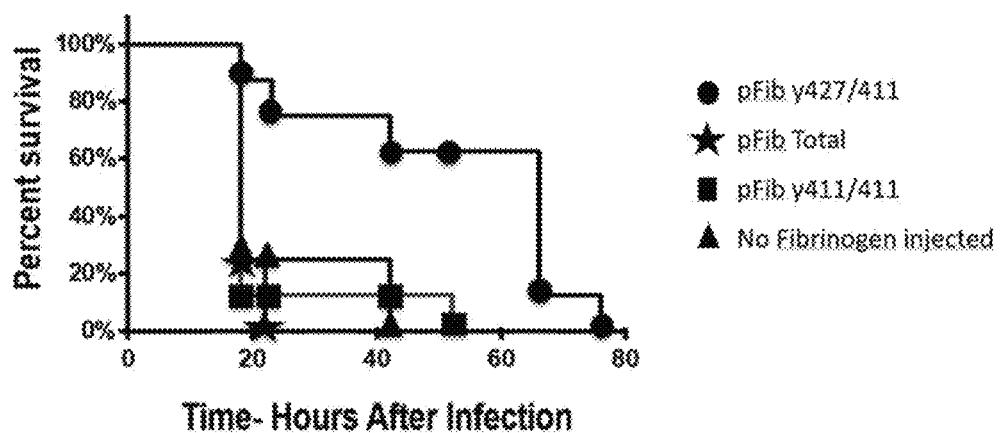
FIG. 8B shows survival profiles of fibrinogen deficient mice (Fib⁻/⁻) supplemented with a single dose of different human fibrinogen species from plasma before a challenge with 1.0×10⁹ CFU *S. aureus* USA 300 WT.
Figure 9:
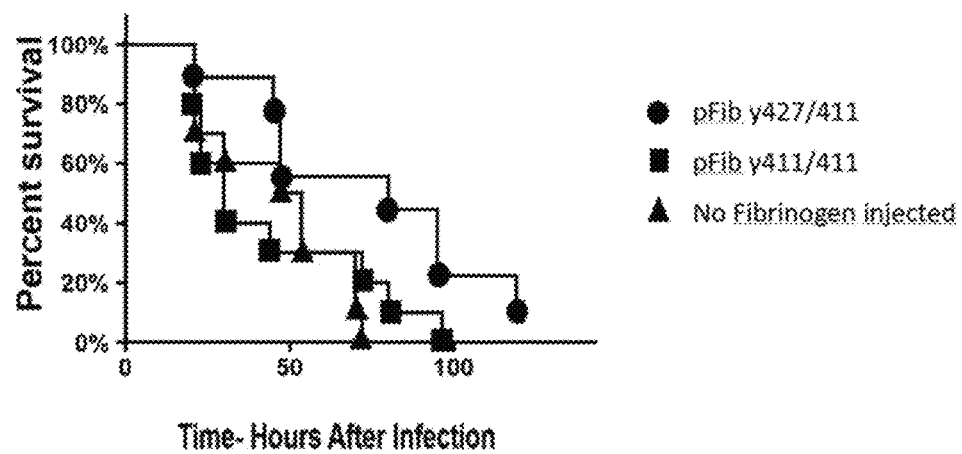
FIG. 9 Survival profiles of fibrinogen WT mice supplemented with a single dose of pFib γ427/γ411 and pFib γ411/411 before a challenge with 3.2×10⁸ CFU *S. aureus* USA 300 WT.
Figure 10:
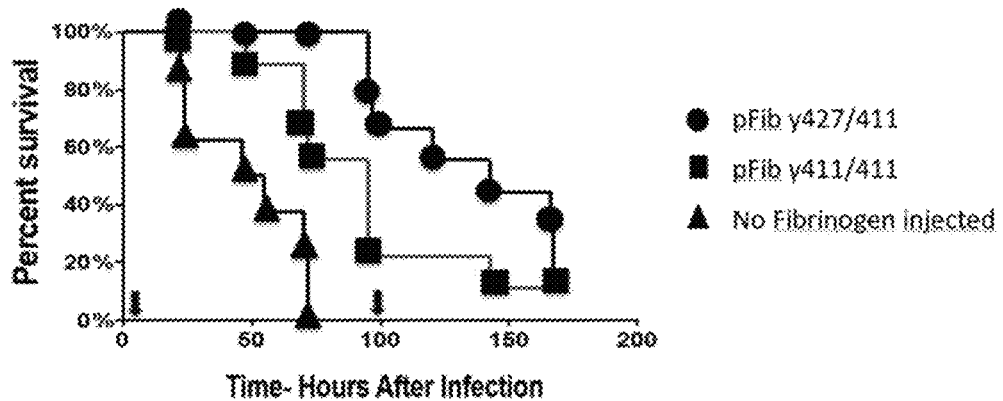
FIG. 10 Survival profiles of fibrinogen deficient mice supplemented with repeated dose of pFib γ427/γ411, as compared to pFib γ411/411 after a challenge with 6.0×10⁸ CFU *S. aureus* USA 300 WT.

FIG. 8A shows that more than 50% of the animals in the group injected with 6 mg of pFib γ411/411 died within 16 hours after the challenge with the S. aureus bacteria. In the group injected with 6 mg pFibγ427/411 this took longer than 48 hours. Replacement of 50% of the ClfA binding site in the carboxyl-terminal end of the fibrinogen gamma chain (AGDV) with the 20 mer of SEQ ID No. 2 seems to provide a 2-3 fold increase in survival time (see also example 10). This could not be expected from literature or from the results for the Fibγ wt/Δ5 in example 6.

FIG. 8B shows that more than 70% of the animals injected with PBS (control), 3 mg pFib total or 3 mg pFib γ411/411 died within 16 hours after the challenge with the *S. aureus* bacteria. Very surprisingly, of the animals injected with 3 mg pFibγ427/411, more than 70% died only after period of 68 hours. This strong increase in survival time following the high dose *S. aureus* infection was highly surprising in view of the small increase in survival time observed with Fib $\gamma^{WT/\Delta5}$ mice at a moderate dose (FIG. 7B) and the absence of any survival advantage in Fib $\gamma^{WT/\Delta5}$ mice at the high dose of *S. aureus* (FIG. 7C). Therefore, the survival effect of the pFib γ 427/411, in which the AGDV motif is replaced by a 20 mer peptide (SEQ ID NO. 2) seems be significantly different from and greater than the survival effect of the delta 5 fibrinogen in which the QAGDV motif is deleted. Without wishing to be bound by theory, it seems that the effect observed with the 20 mer of SEQ ID NO. 2 is only partially related to the inhibition of the interaction of ClfA with its binding motif in the carboxyl-terminal gamma chain of fibrinogen, indicating that the 20 mer sequence could have an additional unexpected and unknown effect on the pathogen or the host, which effect is independent of fibrinogen binding.

Example 8 Prophylactic Treatment of WT Mice with Single Dose of pFib γ427/411 and pFib γ411/411

WT mice (C57Black/6J), age and gender matched, between 8-12 weeks, were administered 6 mg pFib γ411/411 or pFib γ427/411 via tail vein injection. All treatment groups consisted of 10 animals. Infection with *S. aureus* USA 300 WT was also established via tail vein injection. After 30 minutes, the animals were challenged with $3.2\times10^8$ CFU *S. aureus* USA 300 WT strain. Control animals were administered PBS only. The total observation period was 6 days.

FIG. 9 shows that more than 50% of the animals injected with pFib γ411/411 died within 35 hours after the challenge with the *S. aureus* bacteria. Of the animals injected with pFibγ427/411 more than 50% dies after for a period of about 84 hours. This shows that prophylactic treatment of WT mice with a single dose of pFibγ427/411 provides a survival advantage in comparison to type pFib γ411/411. This is highly surprising in view of: 1) the binding and clumping behavior of pFibγ427/411 heterodimer and pFib γ411/411 is very similar and 2) the results also show that pFibγ427/411 heterodimer provides for an increase in survival, despite the presence of the mice own WT fibrinogen. These results indicate that pFibγ427/411 has clinical relevance, since it provides an advantage in survival in the presence of the host's own fibrinogen.

Example 9 Therapeutic Treatment of Fibrinogen Deficient Mice with Repeated Dose of pFib γ427/411 or pFib γ411/411

Fibrinogen deficient mice were first challenged with $5\times10^8$ CFU *S. aureus* USA 300 WT strain and then treated 1-2 hours after infection with a 0.30 ml dose of fibrinogen dissolved in PBS to a concentration of 20 mg/ml (6 mg/animal) followed by a second treatment at 96 hours after infection with the same dose of fibrinogen. 0.3 ml PBS was administered at both treatment time points to the control group.

FIG. 10 shows that more than 50% of the animals injected with PBS (control) died after 60 hours whereas in the group treated with pFib γ411/411>50% died after 92 hours. A surprisingly significant improvement in survival was observed in the group treated with pFib γ427/411 where more than 50% of the animals died after 146 hours. These results indicate that a significant therapeutic effect of pFib γ427/411 on infection with *S. aureus* is still to be expected when administered after the infection has occurred.

Example 10 Survival Time Improvement for Deletion and Substitution of Bacterial Binding Sites Survival time improvements in transgenic mice carrying the delta 5 mutation (ClfA binding site amino acids deleted, not replaced) as reported in Example 6, were compared to prophylactic treatment survival time improvements with pFib γ 427/411 (ClfA binding site amino acids substituted by 20 mer peptide SEQ ID NO. 2) as reported in Example 7 and 8. The relative increase in survival time is calculated from the survival data in examples 6, 7 and 8 by determining the time point at which 50% or less of the treatment and control mice have survived (t≤50%) using the following formula:

$$\frac{(t \leq 50\% \text{ in treatment group}) - (t \leq 50\% \text{ in control group})}{t \leq 50\% \text{ control group}}$$

The results are summarised in Table 1 and show that that survival is improved when the ClfA binding site is not present at the gamma chain. Very surprisingly, survival is significantly higher when the ClfA binding site is replaced by the 20 mer of SEQ ID No. 2 as in pFib γ427/411) than when the binding site is just deleted and not replaced as in Fib γ WT/Δ5 and Fib$\gamma^{\Delta5/\Delta5}$ mice. The presence of the γ427 chain in fibrinogen seems to lead to additional survival time improvement by an unknown mechanism independent of the ClfA binding.

TABLE 1

| | *S. aureus* infection dosage (CFU) | t ≤ 50% survival (hours) | Relative increase t ≤ 50% survival as compared to control (%) |
|---|---|---|---|
| WT mice | 2 × 10E8 | 98 | control |
| Fib γWT/Δ5 mice | | >300 | >200 |
| Fib γΔ5/Δ5 mice | | >300 | >200 |
| WT mice | 6 × 10E8 | 66 | control |
| Fib γWT/Δ5 mice | | 93 | 42 |
| Fib γΔ5/Δ5 mice | | 120 | 83 |
| WT mice | 7 × 10E8 | 33 | control |
| Fib γWT/Δ5 mice | | 45 | 36 |
| Fib γΔ5/Δ5 mice | | 69 | 109 |
| Fib−/− mice + pFib γ411/411 | 5 × 10E8 | 18 | control |
| Fib−/− mice + pFib γ427/411 | | 53 | 192 |
| Fib−/− mice + pFib γ411/411 | 10 × 10E8 | 18 | control |
| Fib−/− mice + pFib γ427/411 | | 66 | 267 |
| WT mice + pFib γ411/411 | 3.2 × 10E8 | 32 | control |
| WT mice + pFib γ427/411 | | 83 | 160 |

The invention claimed is:

1. A method for treating *Staphylococcus aureus* infection, comprising the step of: administering a composition to a human or animal subject having the infection, wherein the composition comprises: a variant fibrinogen having two alpha polypeptide chains, two beta polypeptide chains and two gamma polypeptide chains, wherein at least one of the two gamma polypeptide chains comprises a sequence according to SEQ ID NO. 3, wherein the treatment of the infection results in the reduction of bacterial virulence.

2. The method of claim 1, wherein one of the gamma polypeptide chains comprises a sequence according to SEQ ID NO. 1 and the other gamma polypeptide chain comprises a sequence according to SEQ ID NO. 3.

3. The method of claim 1, wherein the composition comprises not more than about 75% of a WT fibrinogen.

4. The method of claim 1, wherein the variant fibrinogen in the composition is recombinant, plasma-derived, or mixtures thereof.

5. The method of claim 1, wherein the infection is caused by or associated with *Staphylococcus aureus* binding to the carboxyterminus of a fibrinogen gamma chain.

6. The method of claim 5, wherein the *Staphylococcus aureus* is selected from the group consisting of vancomycin resistant *S. aureus*, methicillin-resistant *S. aureus*, and multi-resistant *S. aureus* strains.

7. The method of claim 1, wherein the *Staphylococcus aureus* infection is selected from the group consisting of pneumonia, sepsis, bacteremia, peritonitis, endocarditis, skin or soft tissue infection, osteoarticular infections, prosthetic joint infection, bone infection, pleuropulmonary infection, wound infection, epidural abscesses, meningitis, toxic shock syndrome, urinary tract infection, and septic thrombophlebitis.

8. The method of claim 1, wherein the composition further comprises one or more antibacterials.

9. The method of claim 1, wherein the composition is administered by injection or infusion.

10. The method of claim 1, wherein the composition is administered by an intravenous method, an intra-arterial method, an intraperitoneal method, an intraglandular method, an intravesicular injection, or an infusion method.

11. The method of claim 1, wherein the composition further comprises a pharmaceutically-acceptable carrier.

12. The method of claim 1, wherein the animal is selected from the group consisting of pets, poultry, livestock, sports animals, and rodents.

13. The method of claim 1, wherein the composition is administered in a therapeutically effective amount in the range of 5 mg/kg to 650 mg/kg.

* * * * *